(12) United States Patent
Stanfield et al.

(10) Patent No.: US 11,904,155 B2
(45) Date of Patent: Feb. 20, 2024

(54) HEART ASSIST DEVICE

(71) Applicant: STAR BP, INC., Spring, TX (US)

(72) Inventors: J. Ryan Stanfield, Sandy, UT (US); Michael Vladovich, Oklahoma City, OK (US)

(73) Assignee: STAR BP, INC., Spring, TX (US)

( * ) Notice: Subject to any disclaimer, the term of this patent is extended or adjusted under 35 U.S.C. 154(b) by 546 days.

(21) Appl. No.: 17/168,031

(22) Filed: Feb. 4, 2021

(65) Prior Publication Data
US 2021/0236799 A1 Aug. 5, 2021

Related U.S. Application Data

(63) Continuation of application No. 16/175,795, filed on Oct. 30, 2018, now Pat. No. 10,918,774, which is a (Continued)

(51) Int. Cl.
*A61M 60/148* (2021.01)
*A61M 60/422* (2021.01)
(Continued)

(52) U.S. Cl.
CPC .......... *A61M 60/148* (2021.01); *A61M 60/13* (2021.01); *A61M 60/237* (2021.01);
(Continued)

(58) Field of Classification Search
CPC .. A61M 60/13; A61M 60/148; A61M 60/237; A61M 60/416; A61M 60/422;
(Continued)

(56) References Cited

U.S. PATENT DOCUMENTS 5,211,546 A 5/1993 Isaacson
5,527,159 A 6/1996 Bozeman, Jr.
(Continued)

FOREIGN PATENT DOCUMENTS

CN 101715352 A 5/2010
JP 2010528797 A 8/2010
(Continued)

OTHER PUBLICATIONS

Intellectual Property India, Examination Report dated Jun. 30, 2021, related India patent application No. 201817041180, pp. 1-6, claims examined, pp. 7.
(Continued)

*Primary Examiner* — Christopher A Flory
(74) *Attorney, Agent, or Firm* — EWING & JONES, PLLC

(57) ABSTRACT

A heart assist device comprising a rotary pump housing having a cylindrical bore, a pumping chamber and a motor stator including an electrically conductive coil located within the housing and surrounding a portion of the cylindrical bore. A rotor has a cylindrical shaft with an impeller and one or of magnets located within the shaft that are responsive to the motor stator to drive actuation of the rotor. The housing bore is closely fitted to the outer surface of the shaft forming a hydrodynamic journal bearing with an annular clearance defining a leakage flow path. One or more of radial or axial thrust bearings may be provided to provide rotation stability to the rotor and flow within the leakage flow path. The relative orientation of positions of the inflow, outflow, and leakage flow paths may be varied within the pump, such as to accommodate different intended methods for implantation and/or use.

20 Claims, 14 Drawing Sheets

Related U.S. Application Data continuation of application No. PCT/US2016/030445, filed on May 2, 2016.

(51) Int. Cl.
*A61M 60/824* (2021.01)
*A61M 60/416* (2021.01)
*A61M 60/237* (2021.01)
*A61M 60/13* (2021.01)
*A61M 60/585* (2021.01)
*A61M 60/88* (2021.01)
*A61M 60/857* (2021.01)

(52) U.S. Cl.
CPC ........ *A61M 60/416* (2021.01); *A61M 60/422* (2021.01); *A61M 60/585* (2021.01); *A61M 60/824* (2021.01); *A61M 60/857* (2021.01); *A61M 60/88* (2021.01)

(58) Field of Classification Search
CPC .............. A61M 60/585; A61M 60/824; A61M 60/857; A61M 60/88
See application file for complete search history.

(56) References Cited

U.S. PATENT DOCUMENTS

| | | |
|---|---|---|
| 8,007,254 B2 | 8/2011 | Larose |
| 8,409,276 B2 | 4/2013 | Wampler |
| 8,731,664 B2 | 5/2014 | Foster |
| 9,211,368 B2 | 12/2015 | Wampler |
| 10,918,774 B2 | 2/2021 | Stanfield |
| 2010/0174131 A1 | 7/2010 | Foster |
| 2012/0245404 A1 | 9/2012 | Smith |
| 2013/0183176 A1 | 7/2013 | Wampler |
| 2014/0341726 A1 | 11/2014 | Wu |
| 2015/0051436 A1 | 2/2015 | Spanier |
| 2018/0050139 A1 | 2/2018 | Siess |

FOREIGN PATENT DOCUMENTS

| | | | |
|---|---|---|---|
| JP | 2013212218 A | 10/2013 | |
| JP | 2015508678 A | 3/2015 | |
| WO | 02066838 A1 | 8/2002 | |
| WO | 2008152425 A1 | 12/2008 | |
| WO | 2017192119 | 11/2017 | |

OTHER PUBLICATIONS

ISA/KR, Korean Intellectual Property Office (KIPO), International Search Report and Written Opinion dated Dec. 8, 2016, related PCT international application No. PCT/US2016/030445, pp. 1-12, claims searched, pp. 13-22.

European Patent Office (EPO), Communication (extended European search report) dated Dec. 4, 2019, related European patent application No. 16901122.8, pp. 1-5, claims searched, pp. 6-10.

Japan Patent Office (JPO), official action dated Mar. 10, 2020, related Japanese patent application No. 2018-557314, pp. 1-7, English-language translation, pp. 8-14, claims examined, pp. 15-24.

State Intellectual Property Office of People's Republic of China (SIPO), official action dated Aug. 5, 2020, related Chinese patent application No. 201680085926.2, pp. 1-13, English-language translation, pp. 14-31, claims examined, pp. 32-41.

Japan Patent Office (JPO), Decision of Refusal dated Sep. 14, 2021, related Japanese patent application No. 2018-557314, pp. 1-1, English-language translation, pp. 2-2, Decsion of Dismissal of Amendment, pp. 3-4, English-language translation, pp. 5-6, claims examined, pp. 7-16.

Intellectual Property India, Examination Report dated Jun. 30, 2021, related India patent application No. 201817041180, pp. 1-7, claims examined, pp. 8-17.

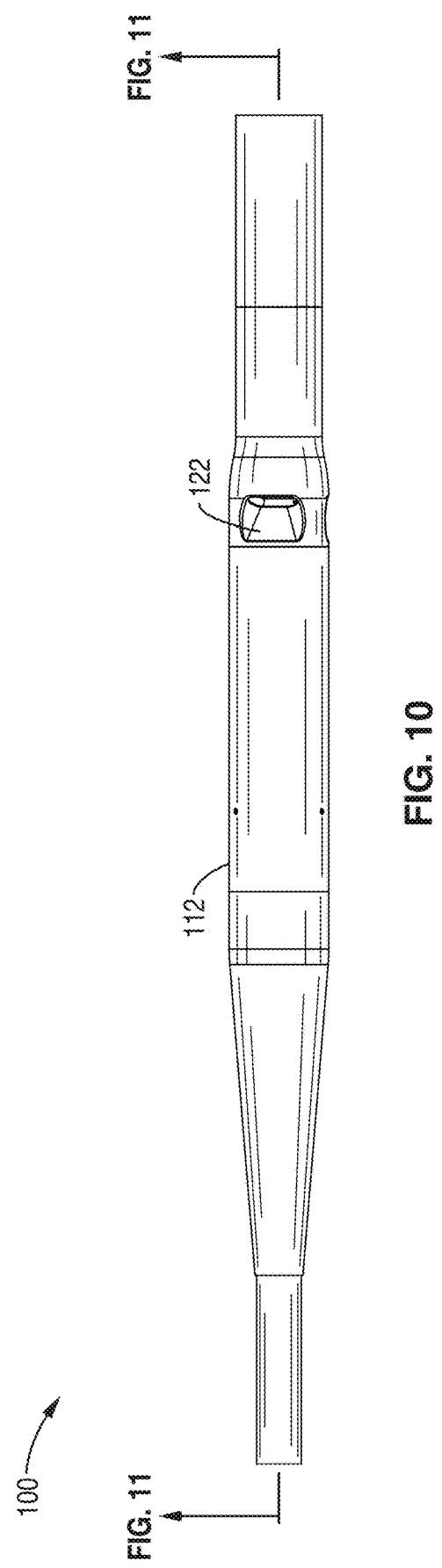

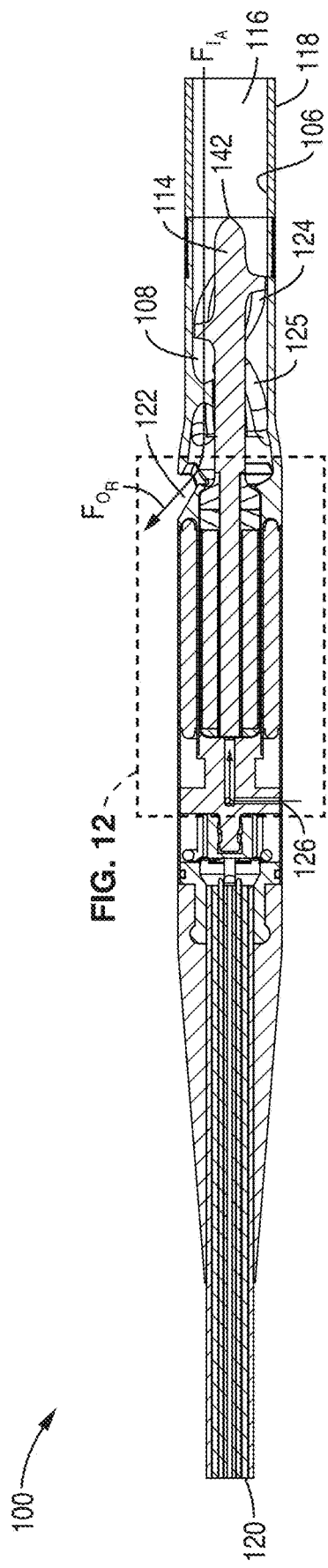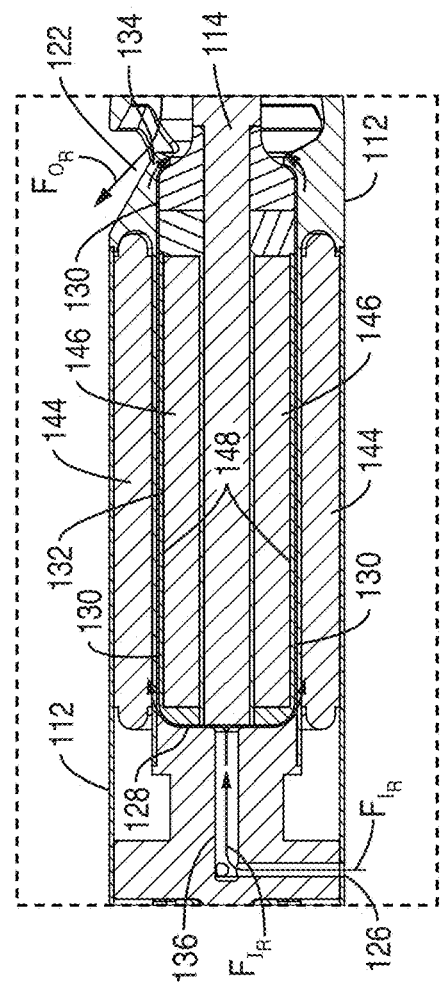

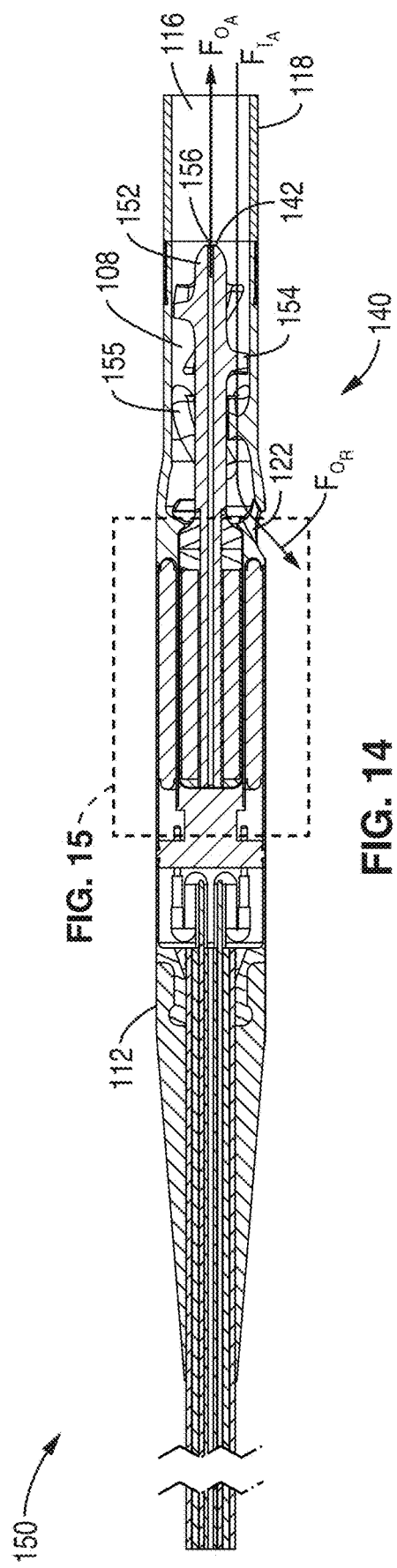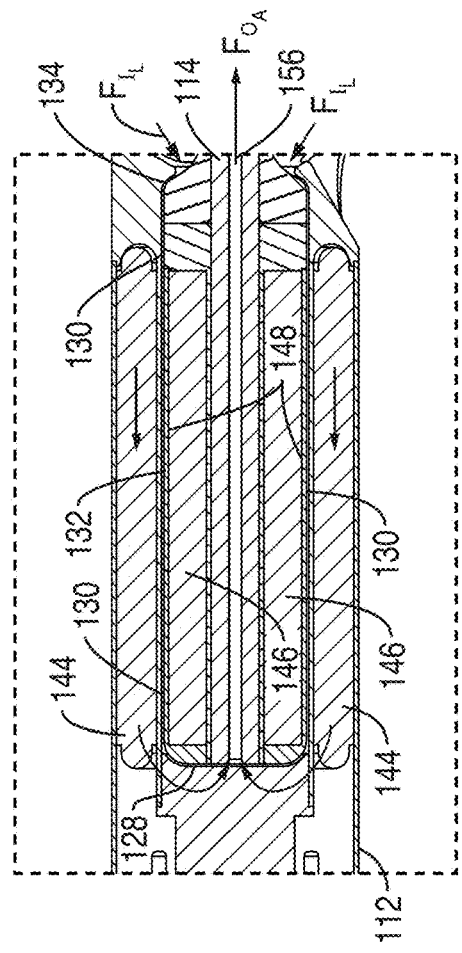
FIG. 14
FIG. 15

HEART ASSIST DEVICE

CROSS-REFERENCE TO RELATED APPLICATIONS

This application is a continuation of U.S. patent application Ser. No. 16/175,795, filed on Oct. 30, 2018 (now U.S. Pat. No. 10,918,774), incorporated herein by reference in its entirety, which claims priority to, and is a 35 U.S.C. § 111(a) continuation of, PCT international application number PCT/US2016/030445 filed on May 2, 2016, incorporated herein by reference in its entirety.

The above-referenced PCT international application was published as PCT International Publication No. WO 2017/192119 on Nov. 9, 2017, which publication is incorporated herein by reference in its entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to methods and devices for assisting the flow of blood through the heart, and more particularly to circulatory assist devices.

2. Background Discussion

Congestive heart failure is a major global public health problem that results in hundreds of thousands of deaths and incalculable human suffering in millions of people each year. Current treatments included modern pharmacologic agents, automatic internal defibrillators and advanced pacing devices including synchronizers. These modalities offer some symptomatic improvement and, potentially, improve survival but all are palliative treatments at best and are not curative.

Existing therapies provide limited clinical benefits for patients in advanced stages of congestive heart failure. In fact, it is estimated that several hundred thousand patients each year with far advanced CHF experience only limited clinical benefit from existing well-established treatments, and could best be served by cardiac transplantation. Cardiac transplantation offers significant improvement in symptoms and survival for patients with end stage heart failure but is available to only a few thousand patients each year due to the limited number of donor hearts.

Mechanical circulatory assistance (MCA), in the form of a total artificial heart (TAH) or a left ventricular assist device (LVAD), has the potential to meet the needs of these patients with end stage heart failure for whom there is little hope. Unfortunately, mechanical circulatory assistance has not developed into a commonly used therapy in the treatment of heart failure.

Historically, there has been substantial evolution in the technology of mechanical circulatory assistance and changes in the paradigms regarding the efficacy of MCA and its role in the treatment of heart failure. The original paradigm envisioned the development of a mass-produced pulsatile TAH that could be implanted routinely in many hundreds of thousands of end stage patients who could otherwise benefit from cardiac transplantation. However, technical challenges have, thus far, precluded the development of the practical TAH needed to achieve the original vision.

Subsequently, it was proposed that LVADs could address the needs of most end stage patients and numerous LVADs have been developed in the last thirty years. Indeed, a number of effective LVADs have shown promise in clinical studies but have experienced only limited commercial success. Such devices include both pulsatile and rotary continuous flow pumps.

Clinical research has shown that LVADs have powerful hemodynamic effectiveness and offer substantial clinical benefit as bridges to cardiac transplantation and in treating post-cardiotomy shock. Recent experience with LVADs for destination therapy in patients who could benefit but are not candidates for cardiac transplantation, has demonstrated improvement in symptoms, quality of life and survival. Significant spontaneous recovery in left ventricular function has been observed in some bridge patients awaiting donor hearts. In some patients who experience spontaneous recovery of left ventricular function, it has been possible to remove the assist device and delay or avoid the need for cardiac transplantation.

Intravascular transvalvular ventricular assistance has been used on a limited basis in patients and has demonstrated significant clinical benefit in the setting of acute cardiogenic shock, failure to wean from cardiopulmonary bypass, assisted high risk angioplasty and, beating heart coronary revascularization. More specifically, two non-thoracotomy methods for achieving central vascular access have been previously described and have been used to a limited extent in patients. These methods are transeptal cannulation of the left atrium and transvalvular cannulation of the left ventricle.

However, previous systems exhibit very limited durability and are not generally considered practical for ambulatory or chronic clinical use.

Mechanical circulatory assistance has been shown to be an effective treatment for patients suffering from severe congestive heart failure (CHF). Both left ventricular assist devices (LVADs) and right ventricular assist devices have been adapted for bridging patients to heart transplantation and for long-term (destination) therapy. Unfortunately, existing methods for inserting these devices require major surgery during which the patient is placed on cardiopulmonary bypass and the heart may be arrested while vascular grafts are connected to a chamber of the heart to provide blood inflow to the pump of the assist system.

The implantation of existing LVADs carries too much risk to justify their customary use except in the most extreme circumstances. Current LVADs require a cardiovascular surgeon and cardiopulmonary bypass for implantation. Many previously disclosed devices and prior efforts require that both the abdominal cavity and the thoracic cavity be opened to implant the pump. Subdiaphragmatic placement of the pump necessitates diaphragmatic penetrations, which is desirable to avoid if possible.

Accordingly, left ventricular assist devices have previously been used only rarely in the treatment of CHF and then as a treatment of last resort. This is highly unfortunate, because LVADs offer greater hemodynamic efficacy than virtually all other adapted treatments, and also offer the potential of much greater clinical benefit in the treatment of congestive heart failure than other therapies and comparable to cardiac transplantation.

The substantial risk associated with present methods of implanting LVADs and RVAD has limited their use to end-stage patients. A much larger group of patients with less severe heart disease are not, presently, considered candidates for treatment with mechanical circulatory assist devices because of the substantial risk of implanting circulatory assist devices.

Thus, there remains a need for improved devices and methods that would permit less invasive cannulation of the chambers of the heart without the need for large incisions, cardiopulmonary bypass and the need to arrest the heart. This would make it possible to better serve large numbers of patients with less severe CHF.

BRIEF SUMMARY

The present disclosure, according to certain aspects, provides methods and devices for minimally and less invasive implantation of mechanical circulatory assist devices. Such a device could find widespread use in the treatment of congestive heart failure, as it can be inserted with minimally or less invasive techniques and be used as an ambulatory chronic ventricular assist device. Use of lower risk minimally or less invasive techniques would make therapeutic ventricular assistance available to class III as well as class IV congestive heart failure patients.

To overcome the barriers and shortcomings incumbent with prior efforts, various aspects of the present disclosure provide new, improved LVADs and the means for their insertion to lower the risk of their use for the treatment of congestive heart failure. These presently disclosed LVADs provide improved safety and simplicity to place in the patient, in particular with minimally and less invasive methods of insertion. According to certain embodiments, LVADs are disclosed which are adapted to be used in the treatment of congestive heart failure by the interventional cardiologist without the need for cardiac surgical support and without the need for a thoracotomy. It is believed that appropriate implementation of the presently disclosed embodiments may become the standard of care in many circumstances. The devices according to further embodiments can be inserted in much the same fashion as the implantable defibrillator, while in certain circumstances perhaps to be supplemented with the aid of a vascular surgeon.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 10 is a side view of a minimally invasive intravascular ventricular assist pump assembly with reversed flow through the bearing.

FIG. 11 is a cross-sectional view of the pump assembly of FIG. 10.

FIG. 12 is an expanded detail view of the cross-sectional view of FIG. 11.

FIG. 14 is a cross-sectional view of the pump assembly of FIG. 13.

FIG. 15 is an expanded detail view of the cross-sectional view of FIG. 14.

DETAILED DESCRIPTION

Figure 1:
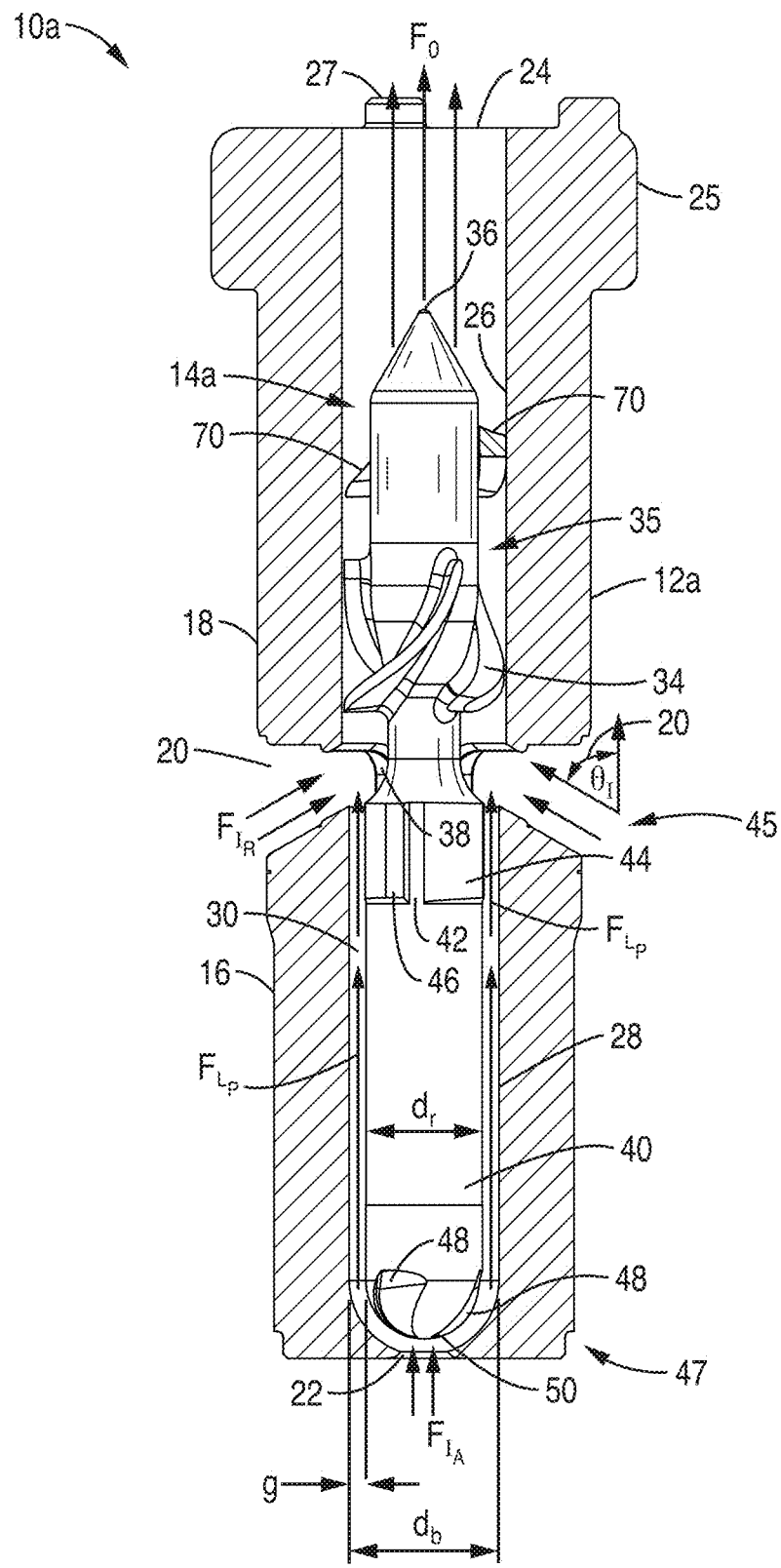
FIG. 1 is a cross-sectional view of a minimally invasive intravascular circulatory assist pump assembly.

Referring more specifically to the drawings, for illustrative purposes the present technology is embodied in the apparatus generally shown in FIG. 1 through FIG. 15. It will be appreciated that the apparatus may vary as to configuration and as to details of the parts, and that the method may vary as to the specific steps and sequence, without departing from the basic concepts as disclosed herein.

FIG. 1 through FIG. 5 show various aspects of a present embodiment minimally invasive intravascular circulatory assist pump assembly 10a that features a pump housing 12a with first and second ends 16, 18, respectively, and a rotor 14a configured to be rotatably disposed within the housing 12a. These components are configured in a particular manner relative to each other as follows.

Housing 12a includes leakage inlet 22 at first end 16, the leakage inlet 22 comprising an axially-located aperture allowing flow $F_{LA}$ into a cylindrical bore 28 that is disposed axially along the length of first end 16. Cylindrical bore 28 is sized such that it forms the mating inner bearing surface to the outer bearing surface 40 of rotor 14*a* via a journal bearing fit between the two surfaces. For purposes of this description, the terms "cylindrical bore 28" and "inner bearing surface" are used interchangeably. Thus, the cylindrical bore 28 and the bearing surface 40 form a hydrodynamic journal bearing, also sometimes referred to as a "fluid" bearing, or "mechanical" bearing or bushing.

The second end 18 of the pump housing 12*a* comprises a cylindrical bore 26, which is configured for housing an impeller 35 of the rotor 14*a*. The impeller 35 generally comprises a plurality of helical sweeping blades 34. The housing 12*a* may also comprise helical stator (diffuser) blades 70 coupled to the inner bore 26. In this configuration, the rotor shaft 14*a* comprises the hub that rotates between the stator blades While a specific configuration and relative arrangement of such impeller 35 and corresponding blades shown in FIG. 1 through FIG. 9 is considered of beneficial use, other configurations may be employed as would be apparent to one of ordinary skill. The combination of the cylindrical bore 26 and impeller 35 operate as a pumping chamber configured to draw blood into and out of the bore 26. For purposes of this description "pumping chamber" and "cylindrical bore" are used interchangeably.

FIG. 1 and FIG. 6 through FIG. 9 show a cylindrical bores 26, 28 with differing diameters, primarily based on preferred sizing of the impeller 35 with respect to the hydrodynamic bearing defined by the rotor outer surface 40 and the inner bearing surface 28. However, it is appreciated that such geometry may be manipulated to optimize the pump to accommodate different applications. Furthermore, it is contemplated that one singular bore may accommodate both the pumping chamber and the inner bearing surface is so desired for ease of manufacturing, or other considerations.

During normal operation of the pump 10*a* as shown in the operating configuration of FIG. 1, rotational motion of the rotor 14*a* within housing 12*a* is generally achieved via a magnetically driven actuator or motor comprising rotor magnets and a rotor stator (both not shown for simplicity) disposed within the bearing surfaces of the rotor 14*a* and housing 12*a* respectively. Representative configurations for such actuator/motor components may be seen with reference to FIG. 10 through FIG. 15, the embodiments of which are described in further detail below.

Upon rotation of the rotor 14*a* within the pump housing 12*a*, the impeller 35 draws blood flow $F_{IR}$ inward from radial port or inlet 20 and into the pumping chamber defined by cylindrical bore 26. Port 20 extends from the outer surface of the housing to the neck of the rotor 14*a*. Blood is directed into radial port 20 at an angle $\Theta_T$ (e.g. 45 degrees) with respect to the longitudinal axis of the rotor 14*a* and bore 26. Thus, the direction of the flow of blood $F_{IR}$ has both a radial and axial component. Thus, for purposes of this discussion "radial port" is herein defined to be a port having at least a radial component with respect to direction of flow. Blood flow progresses from the neck 38 of the rotor 14*a* along the cylindrical bore 26 and past the conical tip 36 of the rotor 14*a* to exit from axial outlet or port 24 as outlet flow $F_o$. Flow $F_{LP}$ is primarily generated by pumping grooves 48 at the location of the axial bearing 47. Furthermore, pressure generated by the impeller 35 also generates some of the motive force flow $F_{LP}$ along an annular leakage or leak path 30 defined by the clearance between the rotor surface 40 and the bore 28 inner wall. Leakage flow path 30 extends from leakage inlet 22 along the hemispherical bottom end 50 (and mating (cupped) inner surface of the bore 28), and then along the length of the cylindrical bore 28 toward port 20.

Axial port 24 may be coupled to a first end of cannula (not shown) with the pump 10*a* located at a first location of the circulatory system, wherein the output flow $F_o$ is dispersed into the first end of cannula for distributing the output flow of blood to a second end of the cannula at a second location in the circulatory system. Correspondingly, it is appreciated that the flow of blood as shown in FIG. 1 may be reversed (e.g. via reversing direction of impeller 35 or orientation of impeller blades 34) such that aperture 24 is an input, and radial ports 20 are an output. Radial flange 25 may be incorporated to provide a number of functions: 1) house motor wires (not shown) for collection and routing out of the pump body through a feedthrough or terminal connection, 2) axial depth locator for affixing the pump housing 12*a* to a tissue wall of the target anatomy, and 3) support coupling of a cannula (not shown) or other conduit. Axial boss 27 may also be provided for axial fixation (i.e. threaded hole) of conduit (not shown).

Radial support of the rotor 14*a* is provided by the action of the relative motion between the outer bearing surface 40 of the rotor 14*a* and the inner bearing surface of cylindrical bore 28 of the pump housing 12*a*. This produces a hydrodynamic radial or journal bearing. In particular, hydrodynamic thrust forces generated by the relative motion of the rotor 14*a* with respect to the inner bearing surface 28 are the primary or sole source of radial suspension of the rotor within the cylindrical bore 28. The journal bearing is sized to form an annular gap g that is a function of the outer diameter dr of the rotor and the inner diameter $d_b$ of the bore. In a preferred embodiment, the annular gap g is sized to be between 0.002 in.-0.003 in. It is appreciated that the image of FIG. 1 shows a much larger gap g for leakage path 30 (respective to the other component dimensions), primarily for illustrating purposes in showing the flow characteristics of the pump 10*a*. The leakage flow paths 30 shown in FIG. 6 through FIG. 9 are more dimensionally accurate depictions component sizing.

The journal bearing construction beneficially minimizes shear stress and promotes leakage flow from the axial leakage inlet 22 toward radial port 20. All mating surfaces are preferably continual relative motion along the communicative leakage path 30. All such tight clearance, low flow surfaces are thus continuously washed with motion, and hemolysis and thrombosis can be minimized. In particular, hemolysis is minimized because $F_{IR} \gg F_{LA}$. The active leakage flow path 30 through moving parts allows active washing of exposed surfaces within the bore 28. This relieves the requirement for seals, which typically aggravate thrombus formation, and thus the present embodiments enhance longevity as an implant.

Figure 2:
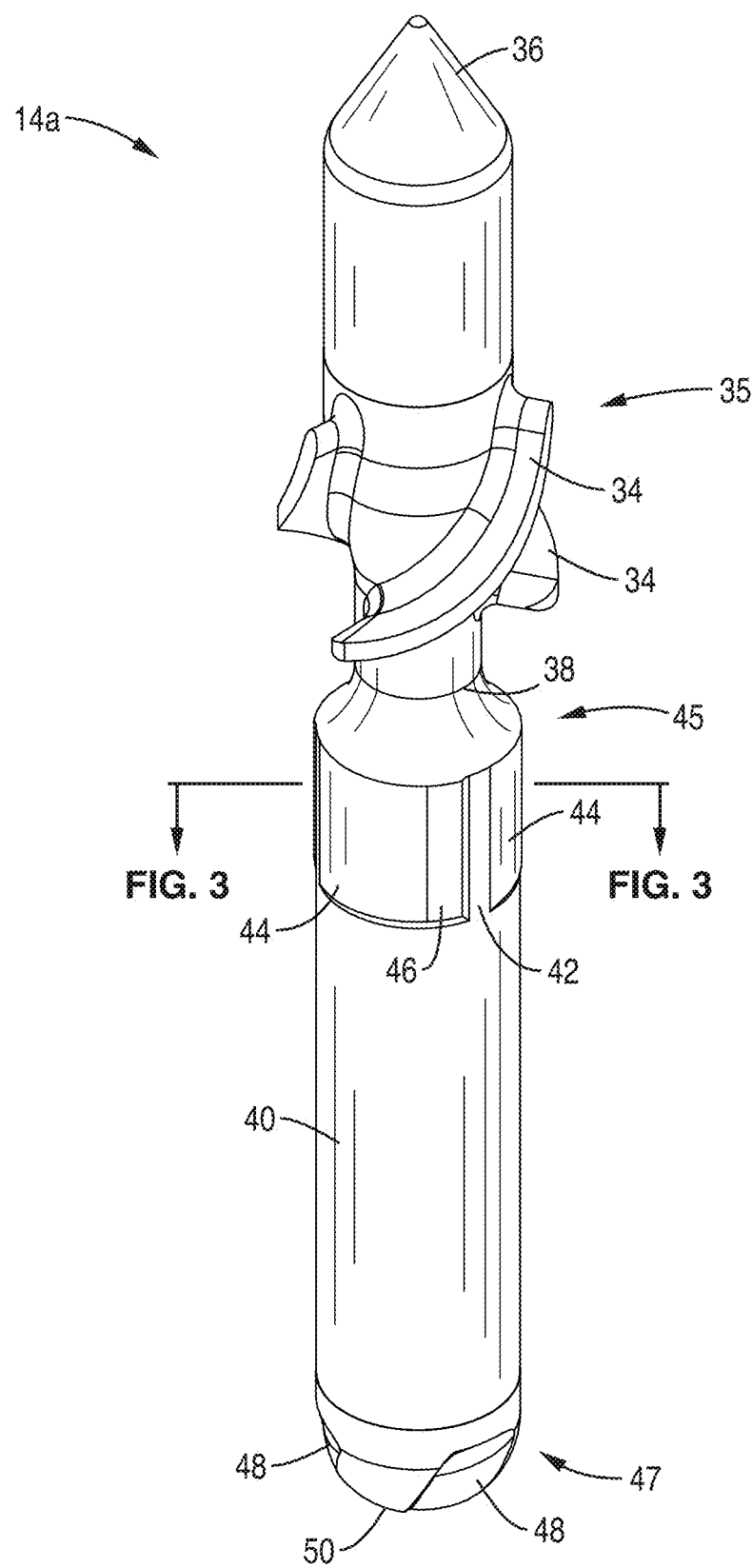
FIG. 2 is a perspective view of a rotor of the pump assembly of FIG. 1, illustrating a tri-lobed tapered land bearing and grooved hemispherical thrust bearing.
Figure 3:
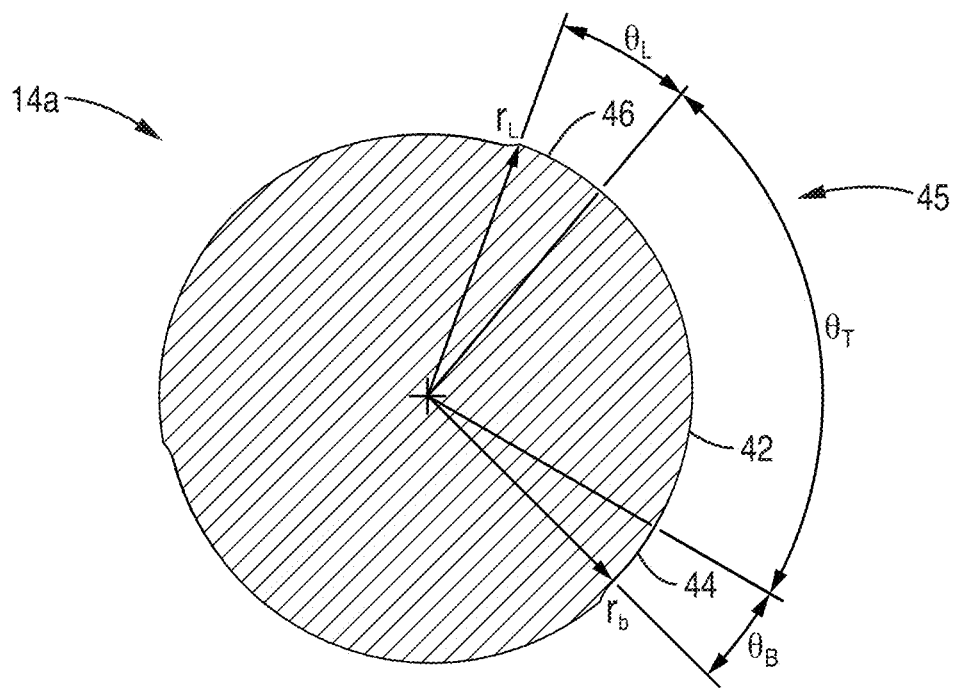
FIG. 3 is a cross-sectional view of the rotor shown in FIG. 2.

As seen in FIG. 1 and in also in the perspective view of the rotor 14*a* in FIG. 2, the pump 10A also comprises a tri-lobed radial bearing 45 and grooved hemispherical thrust bearing 47 to provide additional stability and flow characteristics to the rotor 14*a*. Radial bearing 45 is shown in FIG. 1 at a location adjacent to neck 38 and radial port. As seen in the cross-sectional view of the rotor 10*a* shown in FIG. 3, the radial bearing 45 generally comprises three lands 46 extending outward from a base-diameter section 42. A taper 44 transitions each land 46 and base-diameter section 42. While configurations with different number of lands may be employed, the preferred configuration of radial bearing 45 shown in FIG. 1 through FIG. 4 comprises 3 equally spaced lands 46 approximately 120° apart. The taper sections extends at an angle $\Theta_T$ of approximately 80° along the circumference, while the land section 46 angle $\Theta_L$ and base-diameter section 42 angle $\Theta_B$ extend along approximately 20° of the circumference.

Figure 4:
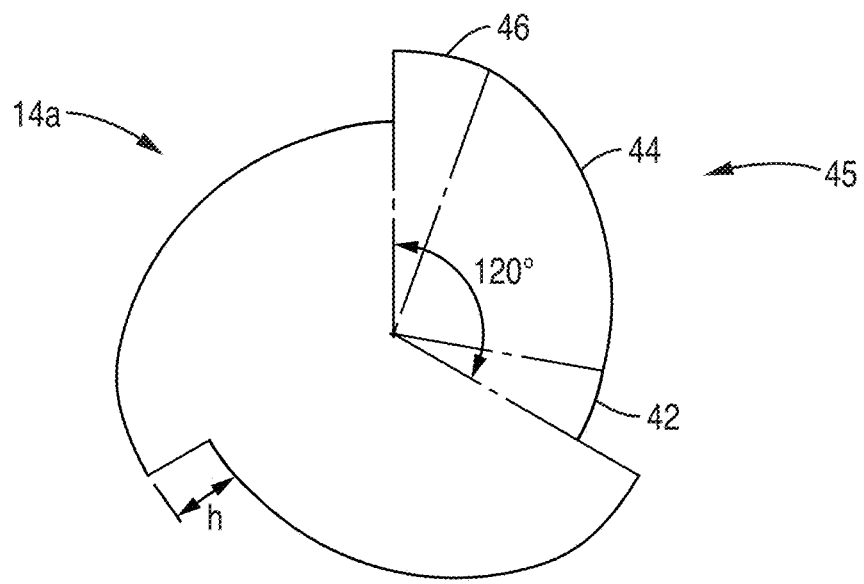
FIG. 4 is a schematic side representation of the rotor cross-section of FIG. 3, illustrating accentuated tapered lands of the radial bearing.
Figure 5:
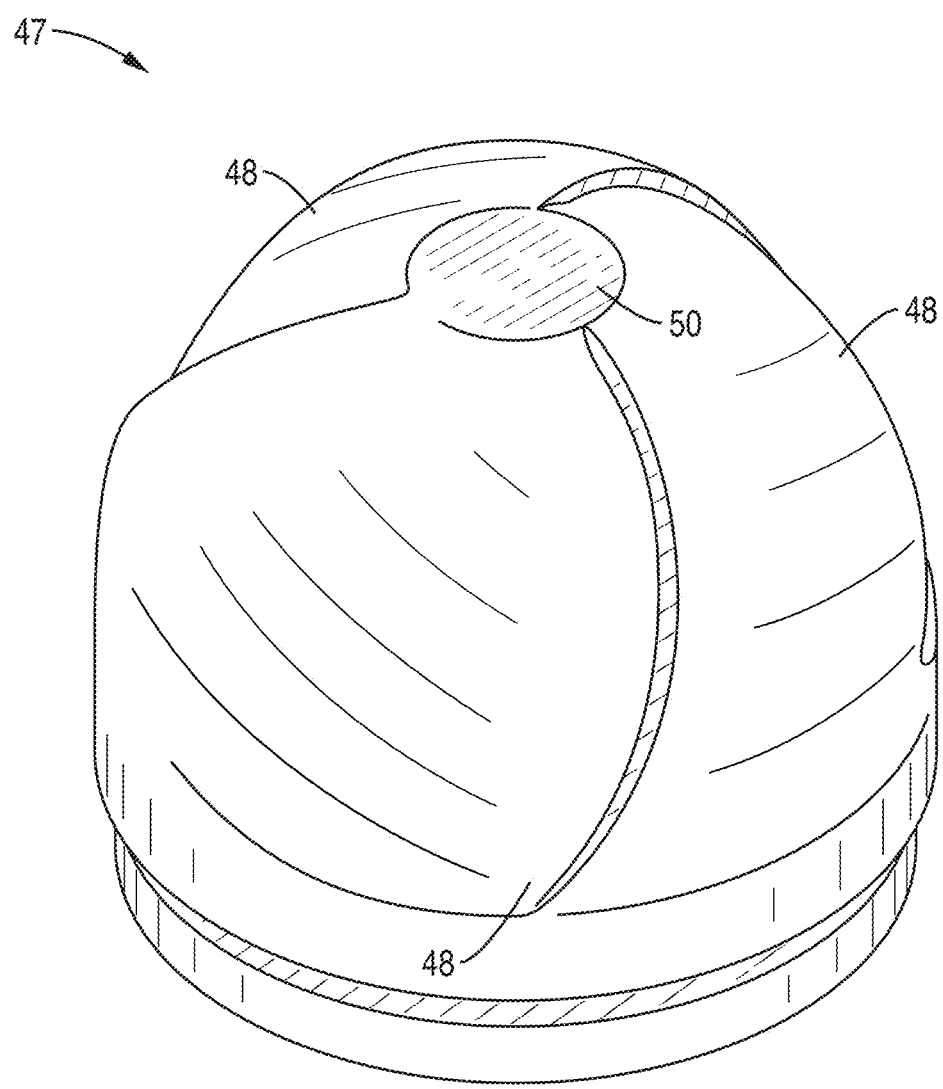
FIG. 5 is a perspective view of the hemispherical thrust bearing of the rotor of FIG. 2.

FIG. 4 shows a schematic side representation of the rotor 14*a* cross-section, accentuated/exaggerating the tapered lands 46 of the radial bearing. The height h of the land, or extent of protrusion from the base diameter 42, is selected for the pressure distribution within the bore 28. Depending on the height h, the diameter of the rotor at base dr may be sized to have a desired gap (e.g. 0.002-0.005 in) according to the diameter of the rotor at the land and the diameter of the cylindrical bore $d_b$. It should be noted that dimension of the diameter of the rotor at the land is representative of 2× the radius $r_L$ shown in FIG. 3, and is an "effective diameter" of the radial bearing 45 while the rotor 14*a* is spinning. It should also be noted that the above dimensions are for illustrative purposes only, and may vary based on pump size and function.

Figure 16:
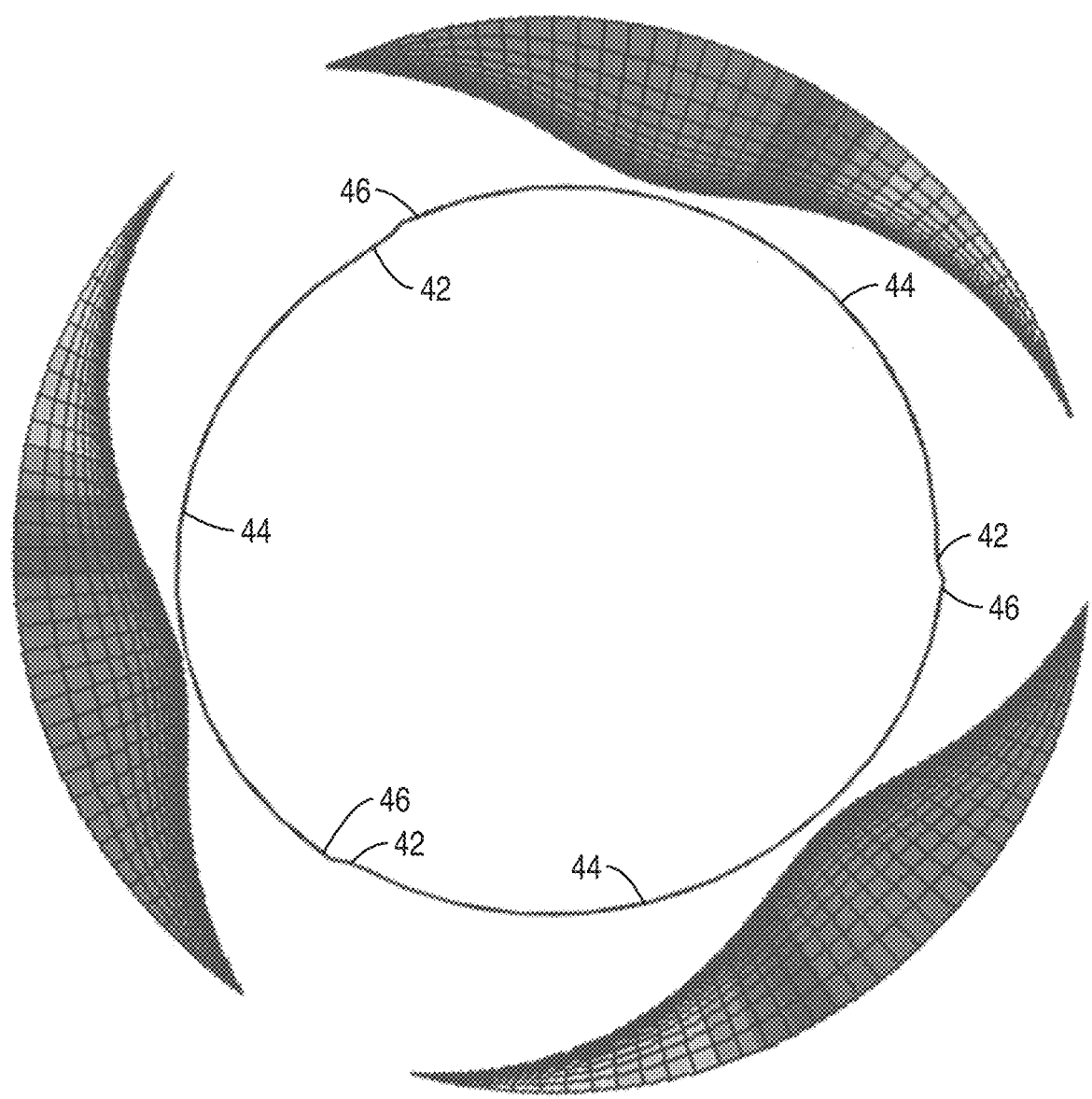
FIG. 16 shows a pressure distribution profile for various points around the radial bearing of FIG. 3.
Figure 17:
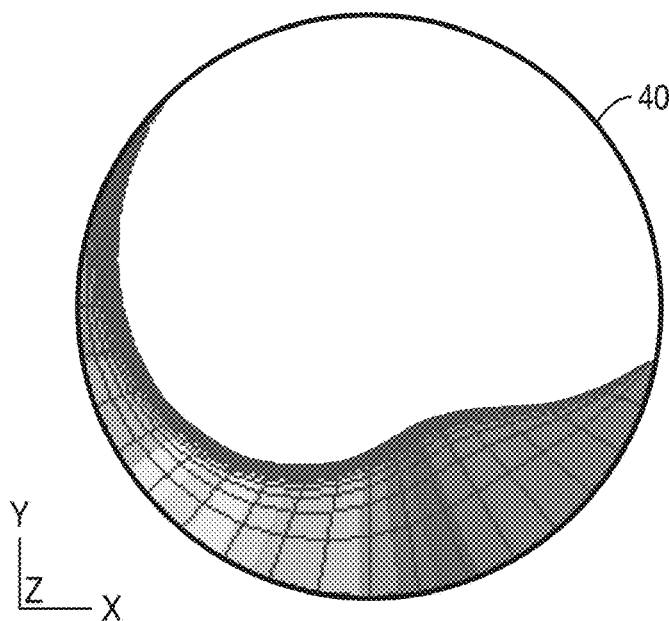
FIG. 17 shows a pressure distribution profile for a plain-sleeve bearing.

Referring now to FIG. 16 and comparatively to FIG. 17, the radial bearing 45, as detailed in the embodiments illustrated in FIG. 1 through FIG. 4 and FIG. 7 through FIG. 9, provides a balanced pressure distribution across the circumference of the rotor 14*a*. FIG. 16 shows a pressure distribution profile for various points around the radial bearing, whereas FIG. 17 shows a pressure distribution profile for a plain-sleeve bearing disposed across outer bearing surface 40, without radial bearing 45.

As can be seen in FIG. 16, moving clockwise around the circumference, pressure is minimal to zero at the base radius section 42, and starts to build at the land 46 and starts to build as the bearing tapers down along tapered section 44. A peak is reached along the tapered, section, then decreases to a minimal or zero pressure prior to the next base radius section 42. The profile then repeats for the remaining two tapered lands. This balanced pressure distribution provides stability to the rotor 14*a* to maintain a substantially centered location within the bore 28, thus maintaining a consistent leakage path 30 around bearing surface 40 at all, or substantially all points around the circumference. Thus, the beneficial fluid flow attributes of the leakage path 30 are beneficially applied to the entirety, or at least vast majority, of the bearing surface and corresponding mating bore 28 surface.

Referring to FIG. 17, a plain sleeve bearing 40 has a pressure distribution that is asymmetric and loaded to one side of the bearing circumference, leading to instability of the rotor 14*a* within the bore 28, and hence instability in the leakage path 30 and corresponding fluid flow characteristics.

While the radial bearing 45 is preferably positioned on the rotor 14*a*, it is appreciated that such a projection may also be positioned on the inner wall of bore 28, with the rotor being a straight sleeve. E.g., the bore 28 may comprise three protrusions in the form of lands extending from a base diameter ($d_b$) section, with three intervening taper sections. However, it is appreciated that due to fabrication difficulties, a rotor-based radial bearing is preferred.

Figure 18:
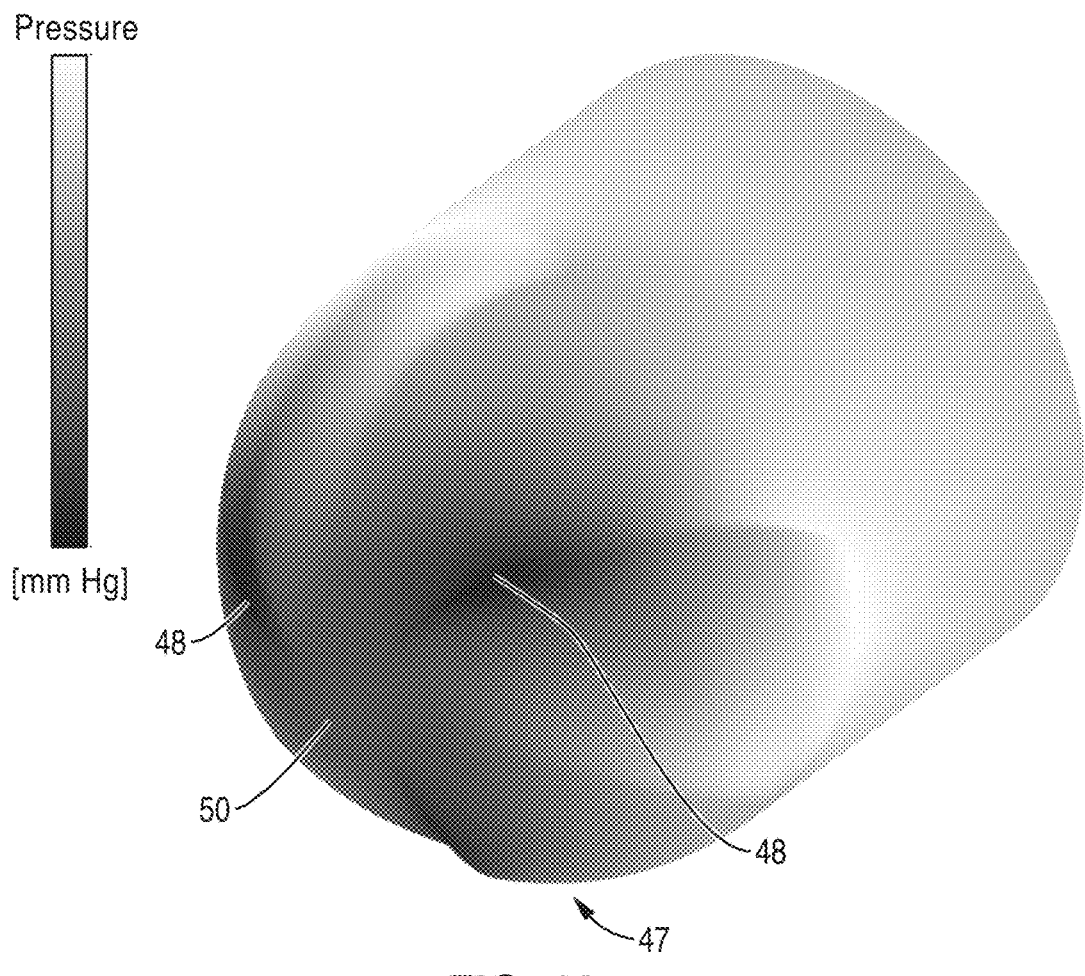
FIG. 18 shows the pressure distribution of the thrust bearing shown in FIG. 5.

Referring back to FIG. 5, a perspective view of the hemispherical thrust bearing 47 disposed at distal end 50 of rotor 14*a* is shown. In this configuration, the axial thrust bearing 47 comprises three swept-tapered grooves 48. The thrust bearing 47 is configured to provide a pressure differential and according pumping mechanism to promote flow through leakage path 30. The grooves 48 are deepest near the center of the arc in a shallow-deep-shallow configuration sweeping from center outward (radially); the low pressure region occurs where the depth is transitioning from shallow to deep FIG. 18 shows the pressure distribution of the thrust bearing 47. As seen in FIG. 18, the pressure is lowest at the distal tip where the depth is transitioning from shallow to deep, and highest (white) at the groove 48 exit, providing significant radial stability. The white regions extend inward as the groove tapers outward translating to axial thrust in the hemispherical or conical configuration. This pressure produces an axial distributed thrust, promoting flow into the leakage path 30, while also providing radial stability as well.

Figure 6:
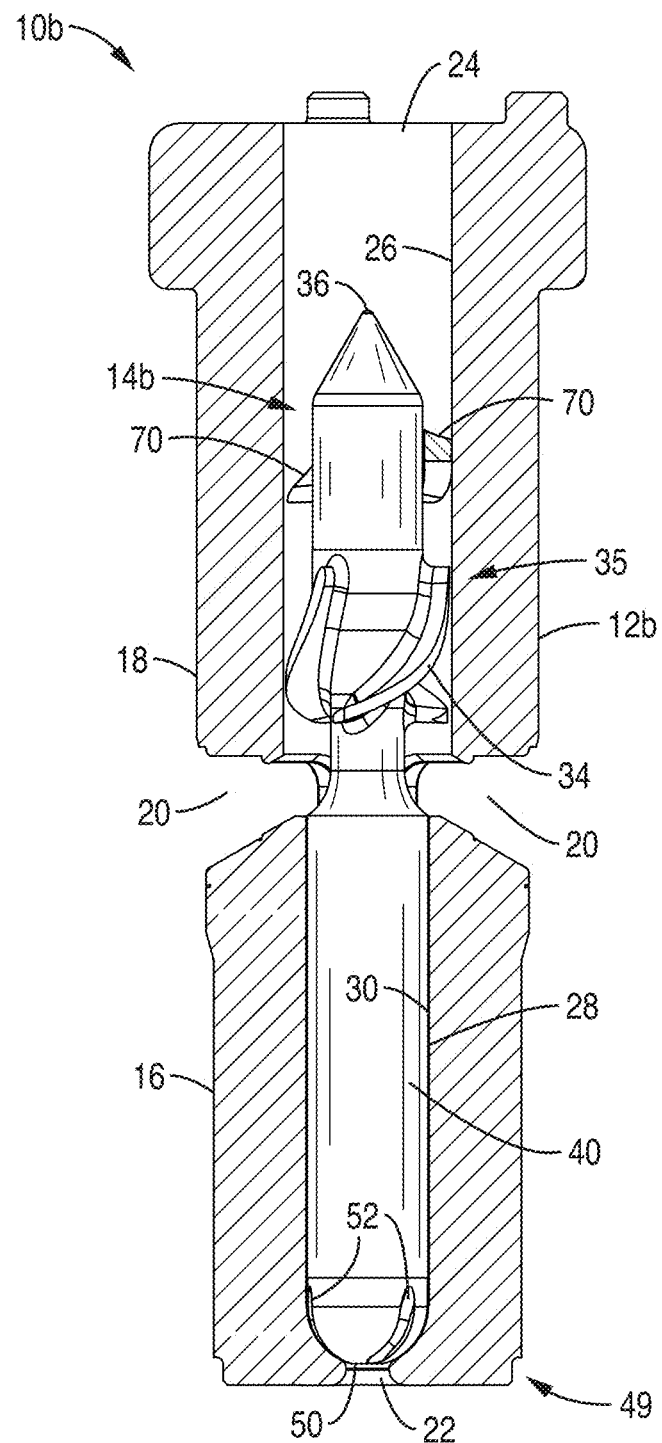
FIG. 6 is cross-sectional view of an alternative minimally invasive intravascular ventricular assist pump assembly having a rotor with a plain-sleeve radial journal bearing and hemispherical axial thrust bearing.

Referring now to FIG. 6, a cross-sectional view of an alternative intravascular ventricular assist pump assembly 10*b* is shown, having a rotor 14*b* with a plain-sleeve radial journal bearing surface 40 and hemispherical axial thrust bearing 49. Pump assembly 10*b* comprises pump housing 12*b* with first and second ends 16, 18, respectively, such that the rotor 14*b* is rotatably disposed within the housing 12*b*.

Housing 12*b* includes leakage inlet 22 at first end 16, the leakage inlet 22 comprising an axially-located aperture allowing flow into a cylindrical bore 28 that is disposed axially along the length of first end 16. Cylindrical bore 28 is sized such that it forms a journal bearing fit with the outside surface of bearing surface 40 of rotor 14*b*.

The second end 18 of the pump housing 12*b* comprises a cylindrical bore 26, which is configured for housing an impeller 35 of the rotor 14*b*. The impeller 35 generally comprises a plurality of axially and radially sweeping blades 24. Upon rotation of the rotor 14*b* within the pump housing 12*b*, the impeller 35 draws flow radially inward from radial port 20 and into the pumping chamber defined by cylindrical bore 26. Blood flow progresses along the cylindrical bore 26 and past the conical tip 36 of the rotor 14*b* to exit from axial outlet or port 24. Flow $F_{LP}$ is primarily generated by pumping grooves 52 at the location of the axial bearing 49. Furthermore, pressure generated by the impeller 35 also generates some of the motive flow along an annular leakage path 30 defined by the clearance between the bearing surface 40 and the bore 28 inner wall. Leakage flow path 30 extends from leakage inlet 22 along the length of the cylindrical bore 28.

A hemispherical thrust bearing 49 is disposed at distal end 50 of rotor 14*b*. In this configuration, the axial thrust bearing 49 comprises three longitudinally oriented grooves 52 that transverse toward the opening 22 from at or near the bearing surface 40. The thrust bearing 49 is configured to provide a pressure differential and according pumping mechanism to promote flow through leakage path 30. It is appreciated that groove 52 and pump assembly 12*b* may be able to generate greater leakage flow; however, there may be greater recirculation present within the deep, longitudinal groove 52 than in the swept-tapered groove 48.

Figure 7:
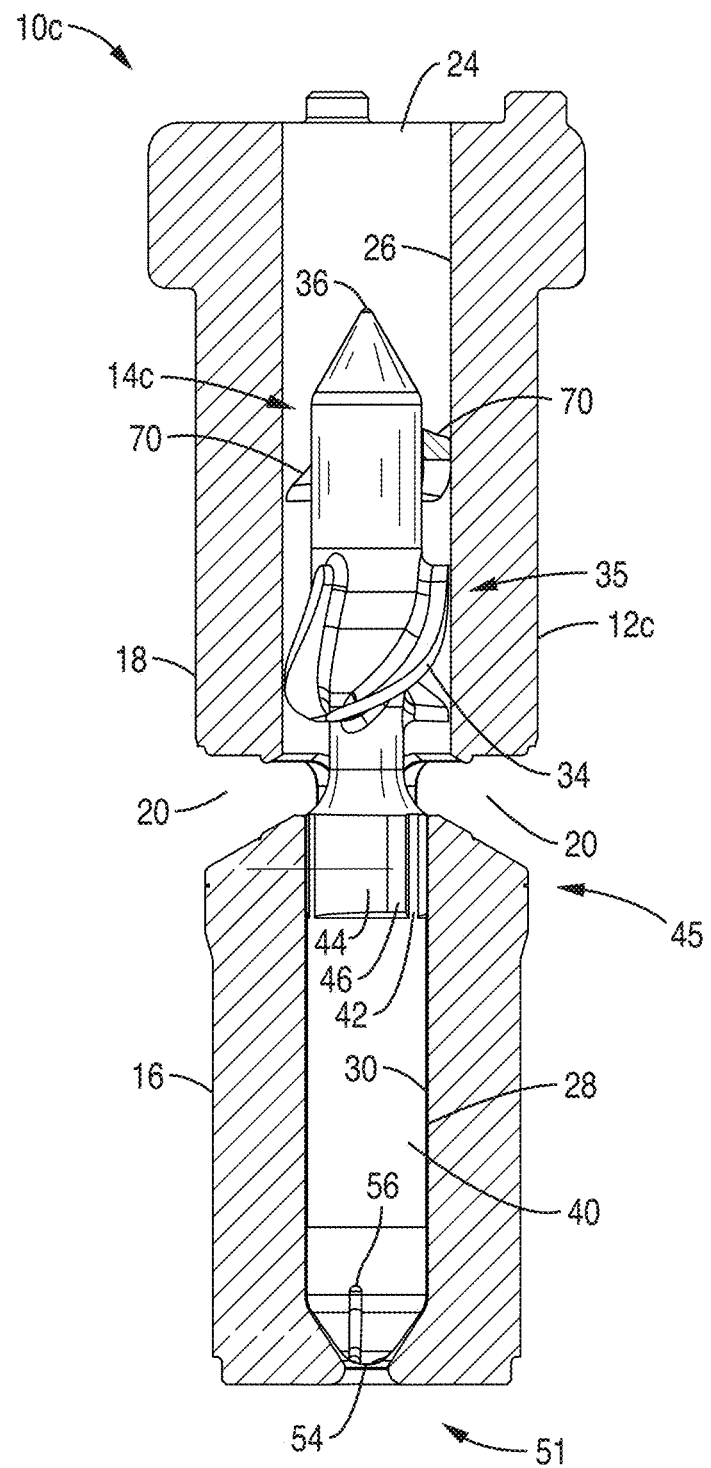
FIG. 7 is cross-sectional view of an alternative minimally invasive intravascular ventricular assist pump assembly having a rotor with a tri-lobed tapered land bearing and conical axial thrust bearing.

FIG. 7 shows a cross-sectional view of an alternative intravascular ventricular assist pump assembly 10*c* having a rotor 14*c* with a tri-lobed tapered land bearing 45 and conical axial thrust bearing 51. Pump assembly 10*c* comprises pump housing 12*c* with first and second ends 16, 18, respectively, with rotor 14*c* configured to be rotatably disposed within the housing 12*c*.

Housing 12*c* includes leakage inlet at first end 16, the leakage inlet comprising an axially-located aperture allowing flow into a cylindrical bore 28 that is disposed axially along the length of first end 16. Cylindrical bore 28 is sized such that it forms a journal bearing fit with the outside surface of bearing surface 40 of rotor 14*c*.

The second end 18 of the pump housing 12*c* comprises a cylindrical bore 26 that is configured for housing impeller 35 of the rotor 14*c*. The impeller 35 generally comprises a plurality of axially and radially sweeping blades 34. Upon rotation of the rotor 14*c* within the pump housing 12*c*, the impeller 35 draws flow radially inward from radial port 20 and into the pumping chamber defined by cylindrical bore 26. Blood flow progresses along the cylindrical bore 26 and past the conical tip 36 of the rotor 14c to exit from axial outlet or port 24. Flow $F_{LP}$ is primarily generated by pumping grooves 56 at the location of the axial bearing 51. Furthermore, pressure generated by the impeller 35 also generates motive force for flow along an annular leakage path 30 defined by the clearance between the bearing surface 40 and the bore 28 inner wall. Leakage flow path 30 extends from leakage inlet 22 along the length of the cylindrical bore 28.

Pump 10c also comprises a tri-lobed radial bearing 45 to provide additional stability and flow characteristics to the rotor 14c. Radial bearing 45 is shown at a location adjacent to neck 38 and radial port. The radial bearing 45 generally comprises three lands 46 extending outward from a base-diameter section 42. A taper 44 transitions each land 46 and base-diameter section 42.

A conical thrust bearing 51 is disposed at conical tip 54 of rotor 14c. In this configuration, the axial thrust bearing 51 comprises three longitudinally oriented grooves 56 that transverse toward the conical tip 54 from at or near the bearing surface 40. The thrust bearing 51 is configured to provide a pressure differential and according pumping mechanism to promote flow through leakage path 30. The conical bearing is similar to the hemispherical bearing in that it can generate both radial and axial forces/pressures with a single set of grooves/features, as opposed to a flat axial bearing (FIG. 8), which may employ one set of tapered-lands in the radial direction and another set of tapered-lands in the axial direction. In some embodiments, a conical axial bearing design may include tapered-land grooves in place of or in addition to longitudinal grooves 56.

A hemispherical bearing may allow more pivoting action (e.g. ball-in-socket joint), where pivoting may be less prevalent with a conical bearing. A conical bearing allows variability of the axial-to-radial force distribution by the angle of the cone.

Figure 8:
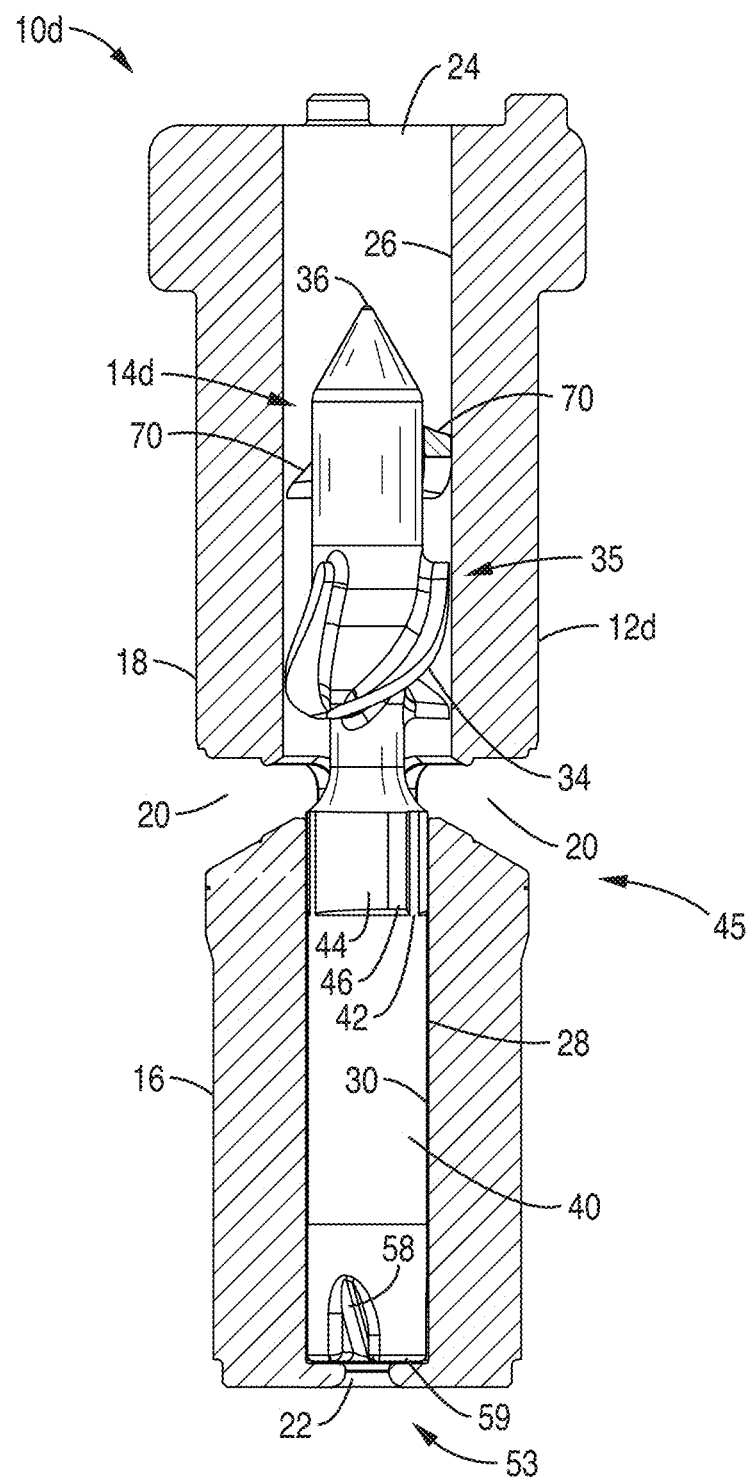
FIG. 8 is cross-sectional view of an alternative minimally invasive intravascular ventricular assist pump assembly having a rotor with a tri-lobed tapered land bearing and flat axial thrust bearing.

FIG. 8 shows a cross-sectional view of an alternative intravascular ventricular assist pump assembly 10d having a rotor 14d with a tri-lobed tapered land bearing 45 and flat axial thrust bearing 53. Pump assembly 10d comprises pump housing 12d with first and second ends 16, 18, respectively, with rotor 14d configured to be rotatably disposed within the housing 12d.

Housing 12d includes leakage inlet 22 at first end 16, the leakage inlet 22 comprising an axially-located aperture allowing flow into a cylindrical bore 28 that is disposed axially along the length of first end 16. Cylindrical bore 28 is sized such that it forms a journal bearing fit with the outside surface of bearing surface 40 of rotor 14d.

The second end 18 of the pump housing 12d comprises a cylindrical bore 26 that is configured for housing impeller 35 of the rotor 14d. The impeller 35 generally comprises a plurality of axially and radially sweeping blades 34. Upon rotation of the rotor 14d within the pump housing 12d, the impeller 35 draws flow radially inward from radial port 20 and into the pumping chamber defined by cylindrical bore 26. Blood flow progresses along the cylindrical bore 26 and past the conical tip 36 of the rotor 14d to exit from radial outlet or port 24. Flow $F_{LP}$ is primarily generated by pumping grooves 58 at the location of the axial bearing 53. Furthermore, pressure generated by the impeller 35 also generates motive force for flow along an annular leakage path 30 defined by the clearance between the bearing surface 40 and the bore 28 inner wall. Leakage flow path 30 extends from leakage inlet 22 along the length of the cylindrical bore 28.

Pump 10d also comprises a tri-lobed radial bearing 45 to provide additional stability and flow characteristics to the rotor 14d. Radial bearing 45 is shown at a location adjacent to neck 38 and radial port. The radial bearing 45 generally comprises three lands 46 extending outward from a base-diameter section 42. A taper 44 transitions each land 46 and base-diameter section 42.

A flat axial thrust bearing 53 is disposed at flat end 59 of rotor 14d. In this configuration, the axial thrust bearing 53 comprises three longitudinally-oriented sweeping-tapered grooves 58 that transverse toward the conical flat end 59. The thrust bearing 53 is configured to provide a pressure differential and according pumping mechanism to promote flow through leakage path 30. The flat bearing may also benefit from two bearing feature sets—one radial and one axial.

Figure 9:
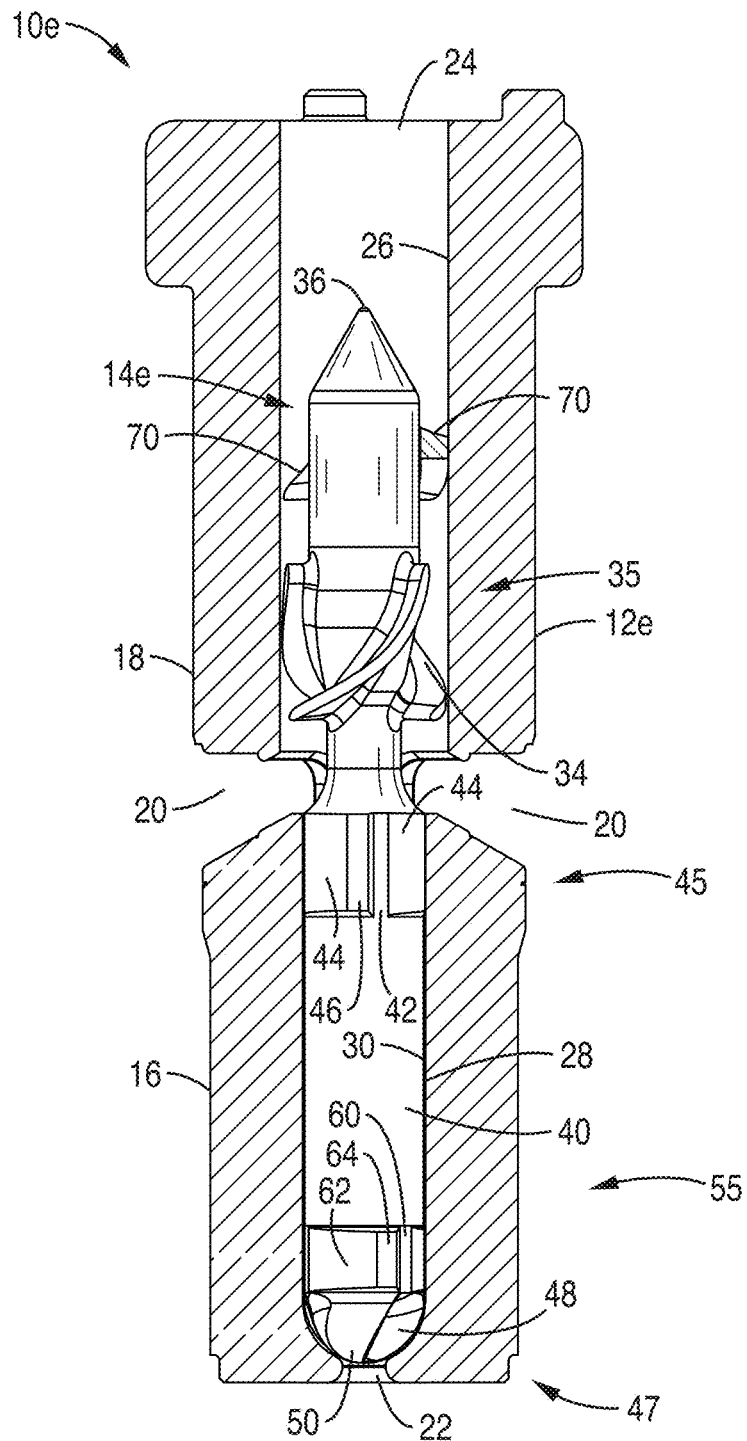
FIG. 9 is cross-sectional view of an alternative minimally invasive intravascular ventricular assist pump assembly having a rotor with forward and aft tri-lobed tapered land bearings and hemispherical axial thrust bearing.

FIG. 9 is cross-sectional view of an alternative intravascular ventricular assist pump assembly 10e having a rotor 14d with a first tri-lobed tapered land bearing 45, a second tri-lobed tapered land bearing 55, and hemispherical axial thrust bearing 47. Pump assembly 10e comprises pump housing 12e with first and second ends 16, 18, respectively, with rotor 14e configured to be rotatably disposed within the housing 12e.

Housing 12e includes leakage inlet 22 at first end 16, the leakage inlet 22 comprising an axially-located aperture allowing flow into a cylindrical bore 28 that is disposed axially along the length of first end 16. Cylindrical bore 28 is sized such that it forms a journal bearing fit with the outside surface of bearing surface 40 of rotor 14e.

The second end 18 of the pump housing 12e comprises a cylindrical bore 26 that is configured for housing impeller 35 of the rotor 14e. The impeller 35 generally comprises a plurality of axially and radially sweeping blades 34. Upon rotation of the rotor 14e within the pump housing 12e, the impeller 35 draws flow radially inward from radial port 20 and into the pumping chamber defined by cylindrical bore 26. Blood flow progresses along the cylindrical bore 26 and past the conical tip 36 of the rotor 14e to exit from axial outlet or port 24. Flow $F_{LP}$ is primarily generated by pumping grooves 48 at the location of the axial bearing 47. Furthermore, pressure generated by the impeller 35 also generates motive force for flow along an annular leakage path 30 defined by the clearance between the bearing surface 40 and the bore 28 inner wall. Leakage flow path 30 extends from leakage inlet 22 along the length of the cylindrical bore 28.

Like the embodiment 10a shown in FIG. 1, pump 10e comprises a tri-lobed radial bearing 45 to provide additional stability and flow characteristics to the rotor 14e. Radial bearing 45 is shown at a location adjacent to neck 38 and radial port. The radial bearing 45 generally comprises three lands 46 extending outward from a base-diameter section 42. A taper 44 transitions each land 46 and base-diameter section 42.

In addition, to radial bearing 45 at the neck region 38 of rotor 14e, a second radial bearing 55 is disposed adjacent or near the hemispherical end 50. Radial bearing 55 generally comprises three lands 64 extending outward from a base-diameter section 60. A taper 62 transitions each land 64 and base-diameter section 60. The second or aft radial bearing 55 operates in a similar or identical fashion as first or forward radial bearing 45 to provide rotational stability to the rotor 14e.

A hemispherical thrust bearing 47 is also disposed at hemispherical end 50 of rotor 14e. In this configuration, the axial thrust bearing 47 comprises three swept-tapered grooves 48. The thrust bearing 47 is configured to provide a pressure differential and according pumping mechanism to promote flow through leakage path 30. This pressure produces an axial distributed thrust, promoting flow into the leakage path 30, while also providing radial stability as well.

FIG. 10 through FIG. 12 show a minimally invasive intravascular ventricular assist pump assembly 100 with reversed bearing flow. FIG. 10 shows a side view of the pump assembly 100, while FIG. 11 is a cross-sectional view of the pump assembly 100. FIG. 12 shows an expanded detail view of the cross-sectional view of FIG. 11.

Pump assembly 100 employs a rotor 114 with integral attachment of the solid rotor shaft to helical blades 124 of impeller 140 (stator blades 125 may also be included on the housing), and operates with similar principles of hydrodynamic suspension as shown and described by the preceding embodiments. The solid rotor 114 comprises rotor magnets 146 that interact with motor stator 144. Motor stator 144 comprises an electrically conductive coil (not shown) that is adapted to be coupled to a power source (not shown) via leads 120, and is positioned relative to the rotor magnet 146 to form a flux gap motor interface such that, in an operating mode upon activation by the power source, electrical current flow through the motor stator 144 coil creates a magnetic flux field that extends across a flux gap clearance (i.e. leakage path 130) between the rotor 114 and housing 112 and that displaces the rotor magnet 146 sufficient to torque the rotor 114 and rotate the rotor 114 within the journal bearing clearance 130 and bore 106 of end 118 of housing 112. It is also appreciated that the motor stator coil 144 may be axially offset with respect to the rotor magnet 146 to form an axial force or preload of the rotor end into the bore of the housing.

It is appreciated that the rotor magnet/rotor stator configuration shown in FIG. 11 and FIG. 12 may similarly be implemented for providing rotor motion for any of the pump embodiments 10a through 10e shown in FIG. 1 through FIG. 9. Motor detail was not included in FIG. 1 through FIG. 9 to allow for highlight the radial and thrust bearing configurations and flow characteristics. It is also appreciated that motor configurations detailed in U.S. Pat. No. 8,409,276, issued on Apr. 2, 2013 (herein incorporated by reference in its entirety) may be used where appropriate on the embodiments of the present description.

Rotation of rotor 114 is supported within bore 132 of housing 112 via a hydrodynamic journal bearing formed from outer surface 148 of the rotor 114, the inner surface of bore 132, and a journal bearing clearance defined by leakage path 130 separating the two. It is appreciated that leakage path 130 is sized to form the journal bearing clearance similar to leakage path 30 of the pumps 10a through 10e shown in FIG. 1 through FIG. 9. It is appreciated that in all embodiments described herein, the rotor 114 (or any of the rotors 14a through 14e of FIG. 1-FIG. 9) is suspended in the radial direction within said housing 112 either substantially or solely by hydrodynamic thrust forces generated by relative movement of said rotor with respect to and within said pump housing as a function of the journal bearing clearance. While the magnetic components (e.g. stator 144 and magnet 146) may incidentally provide some form of suspension (i.e. magnetic suspension), such magnetic suspension is trivial to, and of little effect on, the hydrodynamic thrust forces generated as a function of the journal bearing configuration.

Upon rotation of rotor 114, impeller 140 draws axial input flow $F_{IA}$ through opening or port 116 at end 118 of housing 112, past rotor tip 142 and into pumping chamber 108 defined by bore 106. Propelled fluid then flows radially outward as $F_{OR}$ through radial ports 122. It is appreciated that ports 122 are oriented such that the output flow $F_{OR}$ exits with a radial and axial component (e.g. 45 degrees) with respect to the longitudinal axis of the rotor 114 and housing 112.

Concurrently with radial output flow $F_{OR}$ and axial input flow $F_{IA}$, radial input flow $F_{IR}$ is input from a radial aperture 126 opposite the impeller 140 and pumping chamber 108 from the radial output ports 122. The input flow $F_{IR}$ is fed into an axial channel 136 and dispersed along aft end 128 of rotor 114 (which shares a similar clearance with the aft wall of chamber 132 as rotor bearing surface 148). Flow $F_{LP}$ is driven along the leak path 130 by geometry (i.e. pumping grooves) at 128 and/or 134. The direction of leak path flow $F_{LP}$ can be reversed (from that depicted in this embodiment) based on the geometry at 128 and 134, and relative pressures at 122 and 142. Input flow $F_{IR}$ then migrates along the length of leakage path 130, lubricating the journal bearing, before exiting with flow at output ports 122.

Figure 13:
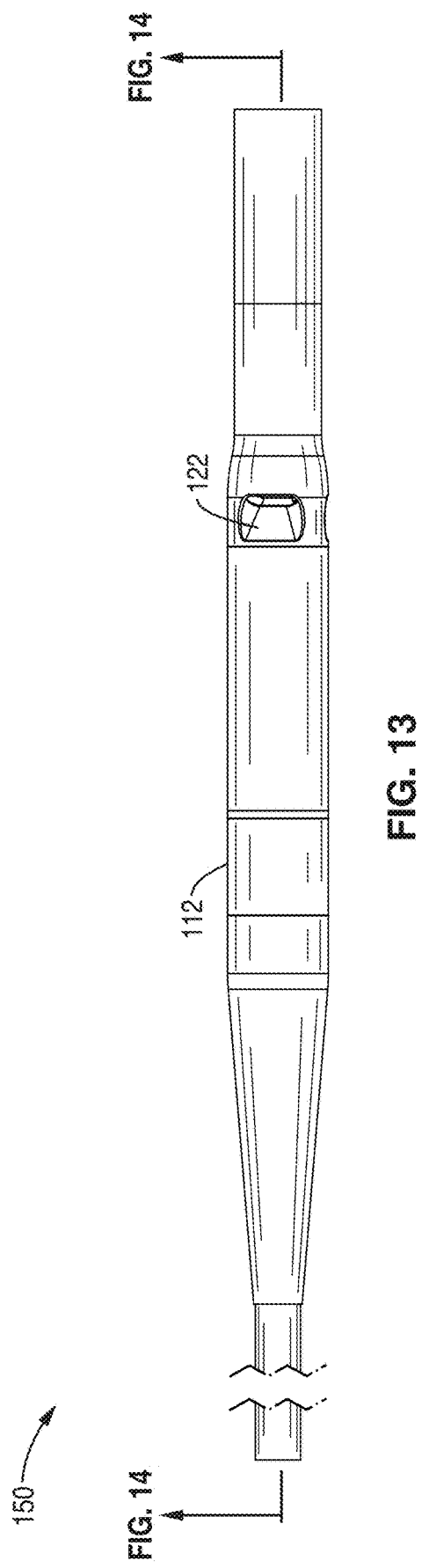
FIG. 13 is a side view of an alternative minimally invasive intravascular ventricular assist pump assembly with reversed flow through the bearing.

FIG. 13 through FIG. 15 show a minimally invasive intravascular ventricular assist pump assembly 150 with reversed bearing flow. FIG. 13 shows a side view of the pump assembly 150 while FIG. 14 is a cross-sectional view of the pump assembly 150. FIG. 15 shows an expanded detail view of the cross-sectional view of FIG. 14.

Pump assembly 150 employs a rotor 114 with integral attachment of the solid rotor shaft to helical blades 154 of impeller 140 (stator blades 155 may also be included on the housing), and operates with similar principles of hydrodynamic suspension as shown and described by the preceding embodiments. The rotor 114 comprises a central channel 156 and rotor magnets 146 that interact with motor stator 144. Motor stator 144 comprises an electrically conductive coil (not shown) that is adapted to be coupled to a power source (not shown), and is positioned relative to the rotor magnet 146 to form a flux gap motor interface such that, in an operating mode upon activation by the power source, electrical current flow through the motor stator 144 coil creates a magnetic flux field that extends across a flux gap clearance (i.e. leakage path 130) between the rotor 114 and housing 112 and that displaces the rotor magnet 146 sufficient to torque the rotor 114 and rotate the rotor 114 within the journal bearing clearance 130 and bore 106 of end 118 of housing 112.

Rotation of rotor 114 is supported within bore 132 of housing 112 via a hydrodynamic journal bearing formed from outer surface 148 of the rotor 114, the inner surface of bore 132, and a journal bearing clearance defined by leakage path 130 separating the two.

Upon rotation of rotor 114, impeller 140 draws axial input flow $F_{IA}$ through port or opening 116 at end 118 of housing 112, past rotor tip 142 and into pumping chamber 108 defined by bore 106. Propelled fluid then flows radially outward as $F_{OR}$ through radial ports 122. It is appreciated that ports 122 are oriented such that the output flow $F_{OR}$ exits with a radial and axial component (e.g. 45 degrees) with respect to the longitudinal axis of the rotor 114 and housing 112.

Concurrently with radial output flow $F_{OR}$ and axial input flow $F_{IA}$, leakage path input flow FIL is input from an annular aperture 134 located at the radial output port 22 and forward extent of the journal bearing. FIL is driven by geometry (i.e. pumping grooves) on the rotor at 134. The direction of leak path flow $F_{LP}$ can be reversed (from that depicted in this embodiment) based on the geometry at 128 and 134, and relative pressures at 122 and 142. The input flow FIL is fed into and migrates along the length of leakage path 130, lubricating the journal bearing, before being dispersed along aft end 128 of rotor 114 (which shares a similar clearance with the aft wall of chamber 132 as rotor bearing surface 148). Input flow $F_{IR}$ then with flows radially inward toward axial central channel 156 where it is then fed along the length of rotor 114 through the central channel 156 where it is output as axial flow $F_{OA}$ at tip 142 of the rotor 114.

A flexible cannula not shown may be attached to the pump body or housing 112 at end 118 of either pump 100 or pump 150. In such configuration, the pump 100/150 would draw input flow $F_{IA}$ of blood from within a first end of cannula, the second end of the cannula being positioned at a different location in the circulatory system. Furthermore, according to an alternative embodiment, different hydraulic pumping elements are employed to reverse the flow direction relative to the cannula and radially displaced flow ports 122. Hence, the aperture 116 at end 118 and first end cannula would be the pump outflow, and the radial slots or ports 122 would serve as the pump inlet.

It is to be appreciated that the various device/pump embodiments of the present disclosure significantly benefit objectives of minimally invasive and less invasive insertion methods are permitted by, as herein described and apparent to one of ordinary skill based upon a comprehensive review of the present disclosure. Two particularly beneficial methods for less invasive surgical implantation are disclosed, though without limitation, and which include: 1) insertion without vascular anastomosis, and 2) insertion with vascular anastomosis.

Minimally invasive insertion is considered of particular benefit to the extent that it allows the implementation of VADs (e.g. LV/LA, or RV/RA) without a thoracotomy or cardiopulmonary bypass. Central vascular access is considered of particular benefit to the extent that it is achieved via peripheral vascular access, such as for example using fluoroscopic guidance, for the placement of either an intravascular pump or specialized cannulas.

Less invasive insertion is considered of particular benefit to the extent that it includes placing the LVAD with a limited surgical incision and without cardiopulmonary bypass. Methods which eliminate the need for vascular anastomoses are furthermore considered very advantageous, and are beneficially achieved according to certain of the present embodiments. Adaptation to an insertion method facilitated by thorascopic techniques further simplifies the procedure, and is also achieved by certain of the present embodiments.

Minimally invasive placement of LVADS is generally considered to fall, predominately, within the domain of the interventional cardiologist (though clearly other adequately trained and capable physicians may practice the present disclosure). Adaptation for use by such interventionalist is provided by certain of the present embodiments, in particular in that such devices generally allow at least one of, and preferably more than one or all of: 1) a simple means for achieving non-thoracotomy vascular access, 2) small cannula systems and miniature pumps suitable for insertion in peripheral arteries, 3) small pumps suitable for subcutaneous implantation on the chest wall, and 4) pumps capable of operating reliably for months to years in an ambulatory setting. An ability to provide minimally or less invasive implantation of LVADs capable of operating reliably in extended ambulatory is a particular benefit presented by certain of the present embodiments and not previously possible by devices and methods of prior disclosures or use.

Various methods are made available by certain present embodiments and which are based on transvascular techniques familiar to the interventional cardiologist. Such methods typically employ placement of a flexible cannula retrograde across the aortic valve to serve as an inflow conduit to a pump. Non-thoracotomy placement of the inflow cannula will typically be via peripheral arterial access. One illustrative method employs placement of a miniature intravascular pump which receives power from an external controller and battery via a percutaneous wire.

For further illustration of one particular method, a pump system is employed that includes a miniaturized pump (e.g. any of pumps 10a through 10e, 100, or 150 illustrated in FIG. 1 through FIG. 15) that is placed within an artery of an arterial system. An inflow cannula is placed retrograde across an aortic valve into left ventricle of heart. The pump outlet (e.g. axial outlet or port 24 in pumps 10a through 10e or port 116 of pump 100 or 150 in reverse flow mode) is positioned in an ascending aorta of the arterial system. Blood is then removed from the left ventricle via the inflow cannula and pumped into the ascending aorta via port 24, thus, directly assisting the left ventricle.

Diastolic heart failure (DHF) may also be assisted by placing the pump inflow in the left atrium (LA) and sending blood to the aorta.

In all embodiments, power may be supplied to the pump 10a through 10e, 100, or 150 via a percutaneous wire (e.g. wiring 120 shown in FIG. 11) from an externally worn motor controller and rechargeable battery system (not shown). In one particular embodiment, the wire is coupled from the external system components to the pump via the subclavian artery. Alternatively, implantable battery and controller may be used, which is powered via transcutaneous electron transfer (TET).

In another embodiment, a system may incorporate the anatomical placement of a pump located in a subcutaneous pouch (not shown) in a pectoral region of a patient. The inflow of the pump (e.g. port 116 shown in FIG. 11) is in continuity with a flexible inflow cannula (not shown) which enters the subclavian artery and traverses retrograde across the aortic valve into the left ventricle. A second outflow cannula connects to the outflow of the pump and returns blood to the arterial system—in this case, via an anastomosis at the contralateral subclavian artery. So configured, blood is removed from the left ventricle and returned to the systemic circulation, thus, directly assisting the left ventricle. As with the previously described system, a percutaneous wire may be used to supply power and/or control to the pump via an externally worn motor controller and rechargeable battery system.

In some embodiments, the pump system, implant configuration, and surgical methods may be conducted without requiring anastomosis of inflow or outflow cannulas to major vessel walls. It is also to be appreciated that these non-anastomotic methods could be adapted to a mini-thoracotomy or thorascopic approach without the need for cardiopulmonary bypass or anastomosis of a vascular graft.

In another embodiment, a pump system employs a pump (e.g. any of pumps 10a through 10e, 100, or 150 illustrated in FIG. 1 through FIG. 15) that is positioned in a left ventricle and with an outlet cannula (e.g. coupled to port 24 of pumps 10a through 10e) that is passed antegrade through the aortic valve. This surgical procedure may be implemented via a small thoracotomy. According to such a method, the pericardium is opened and traction is placed on the ventricular apex. Using puncture techniques and a dilator system, a thin walled trochar is then advanced into the ventricular cavity. The pump, such as a forward flow pump, is then advanced into the left ventricle and the flexible outflow cannula (not shown) is readily advanced antegrade across the aortic valve. The pump is then anchored at the ventricular apex using an anchor assembly, which may be chosen of suitable construction and operation in context with the system and methods described as apparent to one of ordinary skill.

In such configuration, the pump draws blood through ports (e.g. radial inlet port 20 in any of pumps 10a through 10e) in the housing, and pumps the blood forward through the outlet cannula into the supravalvular aorta. The aortic leaflets would generally provide sufficient seal around the outlet cannula.

According to further aspects of a pump system consistent with certain embodiments herein described, less invasive surgical insertion with a vascular anastomosis is performed via a small thoracotomy without cardiopulmonary bypass. Though not herein shown, for further illustration such method may proceed for example as follows.

The pericardium is opened and traction applied to the ventricular apex. Using puncture techniques and a dilator system, a thin walled inflow cannula is inserted into the left ventricle. The outflow graft may be anastomosed to the descending thoracic aorta. Alternatively, the outflow graft could be tunneled to the subclavian or femoral artery for anastomosis. A pump is then placed between the inflow and outflow grafts such that blood is removed from the left ventricle and pumped into the systemic circulation. The pump may be implanted in the thoracic cavity, or subcutaneously, or elsewhere as may be appropriate in a particular case or technique. A percutaneous wire provides power to the pump via an external controller and battery system.

Current left ventricular assist devices generally require surgical cannulation of the left ventricle via the ventricular apex and surgical anastomosis of an arterial graft to the thoracic aorta. The vast majority are too large for placement in the pericardial space or thoracic cavity and are implanted below the diaphragm in the anterior abdomen region.

Subdiaphragmatic placement typically requires tunneling through the diaphragm to route the vascular grafts—this is a big operation and usually requires cardiopulmonary bypass. Placement of the pump in the pericardial space eliminates the need for diaphragmatic penetrations and minimizes the length of the pump inlet. A short pump inlet may reduce the likelihood of thrombus formation in the pump by reducing the amount of work required for pumping.

Various LVAD pump embodiments of the present disclosure are described more fully below. Each is considered to offer certain significant potential advantages over previously disclosed or used systems. Such improvements of the certain embodiments include, without limitation, one or more of the following: simplicity of design, reduction in cost, and reduction of power consumption over existing LVAD designs, and each could readily be adapted to conventional surgical insertion. Moreover, certain embodiments are considered to present the highly beneficial advantage of combining low profile, minimally invasive or less invasive delivery, with longevity of life as extended ambulatory implants.

In addition, the outer diameter and length of the pumps described herein may be readily adjusted to suit an appropriate parameter for a particular application to optimize motor performance and hydrodynamic bearing support for radial constraint of the rotating assembly.

Among other benefits, the pumps of the present description allow for a size envelope that is well suited for insertion into the left ventricular apex or atrium via a mini-thoracotomy and would occupy very little extra-cardiac volume. A vascular graft from the pump outlet would typically be anastomosed to an aorta or a subclavian artery.

The pumps according to the present description may also be constructed small enough that it could be located on the anterior chest wall and receive blood from a transthoracic cannula to the left heart and return flow to the circulation via a graft to the subclavian artery. Access to the left ventricle could also be achieved with a thin-walled cannula placed via the subclavian artery, retrograde across the aortic valve. The aortic valve leaflets would seal around the wall of the cannula. Pressurized flow from the pump outlet could be returned to the circulation via a graft to a peripheral artery such as the subclavian. Such a procedure would be in the domain of the interventional cardiologist.

In one particular further embodiment of use, a pump as detailed in the present description may be inserted into the left ventricular apex or atrium via a mini-thoracotomy, and would occupy very little extra-cardiac volume. A vascular graft from the pump outlet could be anastomosed to the aorta or the subclavian artery. The pump is also small enough that it could be located on the anterior chest wall and receive blood from a transthoracic cannula to the left heart and return flow to the circulation via a graft to the subclavian artery. Likewise, access to the left heart could be achieved with a thin-walled cannula placed via the subclavian artery, retrograde across the aortic valve left and flow returned to the circulation via a graft to the subclavian artery.

The combination of features of the pumps of the present description are generally suited for direct placement in the left ventricle or atria, though radially enlarged features if appropriately constructed or otherwise modified to be collapsed during delivery may allow for more reduced profiles for minimally or less invasive delivery.

In another exemplary embodiment, a proximal end of an outflow cannula (not shown) is coupled to the output (e.g. port 24 of any of pumps 10a through 10e) of the pump, with the distal end inserted through a small hole in the ventricular apex and the outflow cannula passed antegrade across the aortic valve such that the tip of the cannula was above the aortic valve. The aortic valve leaflets would seal around the cannula wall. The outflow cannula could be reinforced or, possibly an inflatable pantaloon design to minimize abrasion of the valve leaflets. The cannula diameter could be much smaller than the pump body. The outer diameter of the outflow cannula as it traverses the aortic valve could be for example approximately 7 mm. The main body of the pump with the pump inlet would remain in the left ventricle. During pump operation blood would be pump from the left ventricle into the supravalvular aorta.

While this disclosure has been described in conjunction with the specific embodiments outlined above, it is evident that many alternatives, modifications and variations will be apparent to those skilled in the art. For example, whereas present embodiments may be described by reference to conductor wires connecting pump motors to external power sources, other power sources or energy coupling mechanisms may be used, such as integral batteries, implanted power sources. Such may further include, for example, implanted batteries that are either integral with the pump assembly or remotely implanted. In various locations, suitable batteries may furthermore have for example fixed charge life, or may be rechargeable, such as via motion actuation or via transcutaneous inductive coupling. According to another example, certain mating or cooperating parts such as rotor magnets and motor stator backirons are shown in specific relative locations to each other according to the specific illustrative embodiments. However, other specific arrangements relative between such components are also contemplated and may also be suitable or even of particular benefit in certain circumstances or applications. For example, whereas the back iron of motor stator embodiments shown is typically shown aligned with the rotor magnet, it may instead be partially longitudinally displaced from the rotor magnet in resting condition. This resting displacement may be configured in order to maximize the displacement force from the magnetic attraction between these components counter-directionally against opposite longitudinal displacement forces incurred by the rotor within the housing when the magnetic flux gap motor is activated.

Furthermore, it is appreciated that features or components of any of the embodiments described herein may be interchangeably used where appropriate. For example, any of the radial or axial bearings detailed in pumps 10a through 10e may be used in the rotor configurations shown in pumps 100 and 150. Furthermore, any of the magnetic drive/actuator components detailed in pumps 100 and 150 may be used in the configurations shown in pumps 10a through 10e.

From the description herein, it will be appreciated that that the present disclosure encompasses multiple embodiments which include, but are not limited to, the following:

1. A heart assist device, comprising: a rotor; said rotor comprising a shaft with an outer surface and an impeller extending from the shaft at a first location on the outer surface; said outer surface comprising an outer bearing surface at a second location on the shaft, and a radial bearing at or adjacent to the outer bearing surface; said radial bearing comprising a plurality of lands protruding radially from the outer bearing surface; wherein the plurality of lands are spaced apart across a circumference of rotor shaft; and a pump housing; the pump housing comprising one or more cylindrical bores configured to define a pumping chamber and an inner bearing surface within the pump housing; wherein, in an operating configuration, the rotor is positioned within the one or more cylindrical bores such that the impeller rotates within the pumping chamber upon actuation of the rotor; wherein said inner bearing surface of the pump housing is closely fitted to said outer bearing surface of said shaft to form an annular clearance there between such that during actuation of the rotor the inner bearing surface and outer bearing surface form a hydrodynamic journal bearing; wherein the pump housing comprises a leakage inlet in fluid communication with the annular clearance; wherein during actuation of the rotor the annular clearance operates as a leakage path to allow the flow of blood into the leakage inlet, and along the length of the annular clearance between the inner bearing surface and outer bearing surface; wherein actuation of the rotor generates a pressure profile within the annular clearance; and wherein the lands of the radial bearing substantially distribute the pressure profile symmetrically across the circumference of the outer bearing surface.

2. The device of any preceding embodiment, wherein said rotor is primarily suspended in the radial direction within said housing by hydrodynamic thrust forces generated by relative movement of said rotor with respect to and within said pump housing.

3. The device of any preceding embodiment: wherein said rotor comprises one or more rotor magnets located within the bearing surface of said shaft; wherein the pump housing comprises a motor stator having a coil positioned opposite said one or more rotor magnets from the annular clearance; and wherein actuation of the rotor is affected by electrical current flow through the motor stator to generate magnetic flux field that extends across the leakage flow path to displace the one or more rotor magnets.

4. The device of any preceding embodiment, wherein the one or more cylindrical bores comprises a first bore disposed at a first end of the pump housing, the first bore defining the inner bearing surface configured for housing the outer bearing surface of the rotor, and a second bore at a second end of the pump housing, the second bore configured for housing the impeller and pumping chamber, the pump housing further comprising: a radial port disposed between the first bore and the second bore; wherein rotation of the impeller draws the flow of blood through the radial port and into the pumping chamber along the length of the second bore and through an outlet disposed at the second end of the pump housing; and wherein the leakage inlet is disposed at an opposite end of the pump housing from the outlet.

5. The device of any preceding embodiment, wherein blood flowing along the leakage path is expelled into the radial port.

6. The device of any preceding embodiment, wherein the each of the plurality of lands gradually taper circumferentially from a base diameter section of the rotor, the base diameter section having a diameter equal to the outer bearing surface.

7. The device of any preceding embodiment, further comprising: an axial bearing disposed at a first end of the rotor; the axial bearing configured to be disposed axially adjacent the leakage inlet of the housing; the axial bearing comprising a plurality of grooves forming a hydrodynamic thrust bearing with a mating surface of the one or more cylindrical bores for opposing axial thrusting of the rotor.

8. The device of any preceding embodiment, wherein the axial thrust bearing is further configured for promoting blood flow into the leakage flow path from the leakage inlet.

9. The device of any preceding embodiment, wherein the axial thrust bearing comprises a hemispherical surface.

10. The device of any preceding embodiment, wherein the plurality of grooves comprises swept-tapered grooves in said hemispherical surface.

11. The device of any preceding embodiment, wherein the axial thrust bearing comprises a conical or flat surface.

12. The device of any preceding embodiment, wherein the radial bearing is disposed on the first end of the outer bearing surface adjacent the radial port, the device further comprising: a second radial bearing comprising a second set of lands protruding radially from the outer bearing surface; wherein the second set of lands are spaced apart across a second circumference of rotor shaft; the second radial bearing disposed on a second end of the bearing surface adjacent the leakage inlet.

13. A heart assist device, comprising: a rotor; said rotor comprising a shaft with an outer surface and an impeller extending from the shaft at a first location on the outer surface; said outer surface comprising an outer bearing surface at a second location on the shaft, and an axial bearing at or adjacent to the outer bearing surface; the axial bearing configured to be disposed axially adjacent the leakage inlet of the housing; and a pump housing; the pump housing comprising one or more cylindrical bores configured to define a pumping chamber and an inner bearing surface within the pump housing; wherein, in an operating configuration, the rotor is positioned within the one or more cylindrical bores such that the impeller rotates within the pumping chamber upon actuation of the rotor; wherein said inner bearing surface of the pump housing is closely fitted to said outer bearing surface of said shaft to form an annular clearance there between such that during actuation of the rotor the inner bearing surface and outer bearing surface form a hydrodynamic journal bearing; wherein the pump housing comprises a leakage inlet in fluid communication with the annular clearance; wherein during actuation of the rotor the annular clearance operates as a leakage path to allow the flow of blood into the leakage inlet, and along the length of the annular clearance between the inner bearing surface and outer bearing surface; and wherein the axial bearing comprises a plurality of grooves forming a hydrodynamic thrust bearing with a mating surface of the one or more cylindrical bores for opposing axial thrusting of the rotor and promoting blood flow into the leakage flow path from the leakage inlet.

14. The device of any preceding embodiment, wherein said rotor is primarily suspended in the radial direction within said housing by hydrodynamic thrust forces generated by relative movement of said rotor with respect to and within said pump housing.

15. The device of any preceding embodiment: wherein said rotor comprises one or more rotor magnets located within the bearing surface of said shaft; wherein the pump housing comprises a motor stator having a coil positioned opposite said one or more rotor magnets from the annular clearance; and wherein actuation of the rotor is affected by electrical current flow through the motor stator to generate magnetic flux field that extends across the leakage flow path to displace the one or more rotor magnets.

16. The device of any preceding embodiment, wherein the one or more cylindrical bores comprises a first bore disposed at a first end of the pump housing, the first bore defining the inner bearing surface configured for housing the outer bearing surface of the rotor, and a second bore at a second end of the pump housing, the second bore configured for housing the impeller and pumping chamber, the pump housing further comprising: a radial port disposed between the first bore and the second bore; wherein rotation of the impeller draws the flow of blood through the radial port and into the pumping chamber along the length of the second bore and through an axial port disposed at the second end of the pump housing; wherein the leakage inlet is disposed opposite the outlet at the first end of the pump housing; and wherein blood flowing along the leakage path is expelled into the radial port.

17. The device of any preceding embodiment, further comprising: a radial bearing at or adjacent to the outer bearing surface; said radial bearing comprising a plurality of lands protruding radially from the outer bearing surface; wherein the plurality of lands are spaced apart across a circumference of rotor shaft; wherein actuation of the rotor generates a pressure profile within the annular clearance; and wherein the lands of the radial bearing substantially distribute the pressure profile symmetrically across the circumference of the outer bearing surface.

18. The device of any preceding embodiment, wherein the each of the plurality of lands gradually taper circumferentially from a base diameter section of the rotor, the base diameter section having a diameter equal to the outer bearing surface.

19. The device of any preceding embodiment, wherein the axial thrust bearing comprises a hemispherical surface.

20. The device of any preceding embodiment, wherein the plurality of grooves comprises swept-tapered grooves in said hemispherical surface.

21. The device of any preceding embodiment, wherein the axial thrust bearing comprises a conical or flat surface.

22. A heart assist device, comprising: a rotor; said rotor comprising a shaft with an outer surface and an impeller extending from the shaft at a first location on the outer surface; said outer surface comprising an outer bearing surface at a second location on the shaft; and a pump housing; the pump housing comprising a first cylindrical bore disposed at a first end of the pump housing, the first cylindrical bore defining an inner bearing surface configured for housing the outer bearing surface of the rotor, and a second cylindrical bore at a second end of the pump housing, the second cylindrical bore configured for housing the impeller; the pump housing further comprising a radial port disposed between the first cylindrical bore and the second cylindrical bore; wherein, in an operating configuration, the rotor is positioned within the first and second cylindrical bores such that the impeller rotates within the pumping chamber upon actuation of the rotor; wherein rotation of the impeller draws the flow of blood through the radial port and into the pumping chamber along the length of the second bore and through an outlet disposed at the second end of the pump housing; wherein said inner bearing surface of the pump housing is closely fitted to said outer bearing surface of said shaft to form an annular clearance there between such that during actuation of the rotor the inner bearing surface and outer bearing surface form a hydrodynamic journal bearing; wherein the pump housing comprises a leakage inlet in fluid communication with the annular clearance, the leakage inlet is disposed opposite the outlet at the first end of the pump housing; and wherein during actuation of the rotor the annular clearance operates as a leakage path to allow the flow of blood into the leakage inlet, and along the length of the annular clearance between the inner bearing surface and outer bearing surface where it is expelled into the radial port.

23. The device of any preceding embodiment, wherein said rotor is primarily suspended in the radial direction within said housing by hydrodynamic thrust forces generated by relative movement of said rotor with respect to and within said pump housing.

24. The device of any preceding embodiment: wherein said rotor comprises one or more rotor magnets located within the bearing surface of said shaft; wherein the pump housing comprises a motor stator having a coil positioned opposite said one or more rotor magnets from the annular clearance; and wherein actuation of the rotor is affected by electrical current flow through the motor stator to generate magnetic flux field that extends across the leakage flow path to displace the one or more rotor magnets.

25. The device of any preceding embodiment, further comprising: a radial bearing at or adjacent to the outer bearing surface; said radial bearing comprising a plurality of lands protruding radially from the outer bearing surface; wherein the plurality of lands are spaced apart across a circumference of rotor shaft; wherein actuation of the rotor generates a pressure profile within the annular clearance; and wherein the lands of the radial bearing substantially distribute the pressure profile symmetrically across the circumference of the outer bearing surface.

26. The device of any preceding embodiment, wherein the each of the plurality of lands gradually taper circumferentially from a base diameter section of the rotor, the base diameter section having a diameter equal to the outer bearing surface.

27. The device of any preceding embodiment, further comprising: an axial bearing at or adjacent to the outer bearing surface; wherein the axial bearing comprises a plurality of grooves forming a hydrodynamic thrust bearing with a mating surface of the one or more cylindrical bores for opposing axial thrusting of the rotor and promoting blood flow into the leakage flow path from the leakage inlet.

28. The device of any preceding embodiment, wherein the axial thrust bearing comprises a hemispherical surface.

29. The device of any preceding embodiment, wherein the plurality of grooves comprises swept-tapered grooves in said hemispherical surface.

30. A heart assist device, comprising: a rotor; said rotor comprising a shaft with an outer surface and an impeller extending from the shaft at a first location on the outer surface; said outer surface comprising an outer bearing surface at a second location on the shaft; and a pump housing; the pump housing comprising a first cylindrical bore disposed at a first end of the pump housing, the first cylindrical bore defining an inner bearing surface configured for housing the outer bearing surface of the rotor, and a second cylindrical bore at a second end of the pump housing, the second cylindrical bore configured for housing the impeller; the pump housing further comprising a radial port disposed between the first cylindrical bore and the second cylindrical bore; wherein, in an operating configuration, the rotor is positioned within the first and second cylindrical bores such that the impeller rotates within the pumping chamber upon actuation of the rotor; wherein rotation of the impeller draws the flow of blood through an axial port disposed at the second end of the pump housing and into the pumping chamber along the length of the second bore to be expelled from the radial port; wherein said inner bearing surface of the pump housing is closely fitted to said outer bearing surface of said shaft to form an annular clearance there between such that during actuation of the rotor the inner bearing surface and outer bearing surface form a hydrodynamic journal bearing; wherein the pump housing comprises a leakage inlet in fluid communication with the annular clearance; and wherein during actuation of the rotor the annular clearance operates as a leakage path to allow the flow of blood into the leakage inlet, and along the length of the annular clearance between the inner bearing surface and outer bearing surface.

31. The device of any preceding embodiment, wherein said rotor is primarily suspended in the radial direction within said housing by hydrodynamic thrust forces generated by relative movement of said rotor with respect to and within said pump housing.

32. The device of any preceding embodiment: wherein said rotor comprises one or more rotor magnets located within the bearing surface of said shaft; wherein the pump housing comprises a motor stator having a coil positioned opposite said one or more rotor magnets from the annular clearance; and wherein actuation of the rotor is affected by electrical current flow through the motor stator to generate magnetic flux field that extends across the leakage flow path to displace the one or more rotor magnets.

33. The device of any preceding embodiment: wherein the leakage inlet is disposed at the first end of the pump housing at an opposite end of the first cylindrical bore from the radial port; and wherein the blood flowing within the leakage path is expelled into the radial port.

34. The device of any preceding embodiment wherein the leakage inlet comprises a radial port that disperses leakage inlet blood flow at one end of the first cylindrical bore.

35. The device of any preceding embodiment: wherein the leakage inlet comprises an annular inlet at or near the radial port; wherein the blood in the leakage path flows along the length of the annular clearance away from the radial port toward an opposite end of the first cylindrical bore from the radial port, and around a first end of the rotor disposed at the opposite end of the first cylindrical bore and into a central channel running axially along the length of the rotor; and wherein the blood flowing within the central channel is expelled from a second end of the rotor into the second cylindrical bore.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A heart assist apparatus, comprising:
  a pump housing having a first end and a second end;
  a rotor retained within said pump housing;
  said rotor comprising a shaft with an outer surface and an impeller extending from the shaft at a first location on the outer surface at a proximal end of said rotor at the first end of said pump housing;
  said outer surface of said rotor comprising an outer bearing surface at a second location on the shaft with a radial bearing at or adjacent to the outer bearing surface comprising a plain-sleeve radial journal bearing surface;
  an axial bearing comprising a hemispherical surface or conical surface disposed axially adjacent a leakage inlet of said pump housing at a distal end of said rotor at the second end of said pump housing and having a plurality of grooves configured for promoting blood flow into a leakage flow path from the leakage inlet;
  said pump housing comprising one or more cylindrical bores configured to define a pumping chamber and an inner bearing surface within the pump housing and a radial port disposed between the pumping chamber and the inner bearing surface;
  wherein, in an operating configuration, the impeller rotates within the pumping chamber upon actuation of the rotor to draw a first flow of blood inward from the radial port into the pumping chamber;
  wherein rotation of the impeller draws a second flow of blood through an axial port, as the leakage inlet, disposed at the second end of the pump housing, into the pumping chamber along the length of the inner bearing surface through a leakage flow path in fluid communication with an annular clearance between the inner bearing surface and outer bearing surface; and wherein said inner bearing surface of the pump housing is closely fitted to said outer bearing surface of said shaft to form the annular clearance there between such that during actuation of the rotor the inner bearing surface and outer bearing surface form a hydrodynamic journal bearing.

2. The apparatus of claim 1, wherein said rotor is primarily suspended in the radial direction within said housing by hydrodynamic thrust forces generated by relative movement of said rotor with respect to and within said pump housing.

3. The apparatus of claim 1:
wherein said rotor comprises one or more rotor magnets located within the bearing surface of said shaft of said rotor;
wherein the pump housing comprises a motor stator having a coil positioned opposite said one or more rotor magnets from the annular clearance; and
wherein actuation of the rotor is affected by electrical current flow through the motor stator to generate magnetic flux field that extends across the leakage flow path to displace the one or more rotor magnets to achieve rotational motion of said rotor.

4. The apparatus of claim 1:
wherein said radial bearing comprises a plurality of lands protruding radially from the inner bearing surface; and
wherein the plurality of lands are spaced apart across a circumference of the cylindrical bore.

5. The apparatus of claim 1, wherein the apparatus is configured so that the flow of blood may be reversed by reversing the direction of the impeller wherein blood is input into said pumping chamber and output through said radial ports.

6. The apparatus of claim 1, wherein said axial bearing is configured to provide additional stability and flow characteristics to the rotor.

7. The apparatus of claim 1, wherein said one or more cylindrical bores of said pump housing comprise two cylindrical bores of differing diameters.

8. The apparatus of claim 1, wherein said radial port is configured having at least a radial component with respect to direction of flow.

9. A heart assist apparatus, comprising:
a pump housing having a first end and a second end;
a rotor retained within said pump housing;
said rotor comprising a shaft with an outer surface and an impeller extending from the shaft at a first location on the outer surface at a proximal end of said rotor at the first end of said pump housing;
said outer surface of said rotor comprising an outer bearing surface at a second location on the shaft with a radial bearing at or adjacent to the outer bearing surface comprising a radial journal bearing surface;
an axial bearing comprising a hemispherical surface or conical surface disposed axially adjacent a leakage inlet of said pump housing at a distal end of said rotor at the second end of said pump housing and having a plurality of grooves configured for promoting blood flow into a leakage flow path from the leakage inlet;
said pump housing comprising one or more cylindrical bores configured to define a pumping chamber and an inner bearing surface within the pump housing and a radial port disposed between the pumping chamber and the inner bearing surface, with said radial port configured to provide at least a radial component with respect to direction of flow;

wherein said impeller is configured for rotating within the pumping chamber upon actuation of the rotor to draw a first flow of blood inward from the radial port into the pumping chamber;
wherein rotation of the impeller draws a second flow of blood through an axial port, as the leakage inlet, disposed at the second end of the pump housing, into the pumping chamber along the length of the inner bearing surface through a leakage flow path in fluid communication with an annular clearance between the inner bearing surface and outer bearing surface; and
wherein said inner bearing surface of the pump housing is closely fitted to said outer bearing surface of said shaft to form the annular clearance there between such that during actuation of the rotor the inner bearing surface and outer bearing surface form a hydrodynamic journal bearing.

10. The apparatus of claim 9, wherein said rotor is primarily suspended in the radial direction within said housing by hydrodynamic thrust forces generated by relative movement of said rotor with respect to and within said pump housing.

11. The apparatus of claim 9:
wherein said rotor comprises one or more rotor magnets located within the bearing surface of said shaft of said rotor;
wherein the pump housing comprises a motor stator having a coil positioned opposite said one or more rotor magnets from the annular clearance; and
wherein actuation of the rotor is affected by electrical current flow through the motor stator to generate magnetic flux field that extends across the leakage flow path to displace the one or more rotor magnets to achieve rotational motion of said rotor.

12. The apparatus of claim 9:
wherein said radial bearing comprises a plurality of lands protruding radially from the inner bearing surface; and
wherein the plurality of lands are spaced apart across a circumference of the cylindrical bore.

13. The apparatus of claim 9, wherein the apparatus is configured so that the flow of blood may be reversed by reversing the direction of the impeller wherein blood is input into said pumping chamber and output through said radial ports.

14. The apparatus of claim 9, wherein said axial bearing is configured to provide additional stability and flow characteristics to the rotor.

15. The apparatus of claim 9, wherein said one or more cylindrical bores of said pump housing comprise two cylindrical bores of differing diameters.

16. A heart assist apparatus, comprising:
a pump housing having a first end and a second end;
a rotor retained within said pump housing;
said rotor comprising a shaft with an outer surface and an impeller extending from the shaft at a first location on the outer surface at a proximal end of said rotor at the first end of said pump housing;
said outer surface of said rotor comprising an outer bearing surface at a second location on the shaft with a radial bearing at or adjacent to the outer bearing surface comprising a radial journal bearing surface;
an axial bearing comprising a hemispherical surface or conical surface disposed axially adjacent a leakage inlet of said pump housing at a distal end of said rotor at the second end of said pump housing and having a plurality of grooves configured for promoting blood flow into a leakage flow path from the leakage inlet;

said pump housing comprising one or more cylindrical bores configured to define a pumping chamber and an inner bearing surface within the pump housing and a radial port disposed between the pumping chamber and the inner bearing surface, with said radial port configured to provide at least a radial component with respect to direction of flow;

wherein said impeller is configured for rotating within the pumping chamber upon actuation of the rotor to draw a first flow of blood inward from the radial port into the pumping chamber;

wherein rotation of the impeller draws a second flow of blood through an axial port, as the leakage inlet, disposed at the second end of the pump housing, into the pumping chamber along the length of the inner bearing surface through a leakage flow path in fluid communication with an annular clearance between the inner bearing surface and outer bearing surface;

wherein said inner bearing surface of the pump housing is closely fitted to said outer bearing surface of said shaft to form the annular clearance there between such that during actuation of the rotor the inner bearing surface and outer bearing surface form a hydrodynamic journal bearing;

wherein the apparatus is configured so that the flow of blood may be reversed by reversing the direction of the impeller wherein blood is input into said pumping chamber and output through said radial ports;

wherein said rotor comprises one or more rotor magnets located within the bearing surface of said shaft of said rotor;

wherein the pump housing comprises a motor stator having a coil positioned opposite said one or more rotor magnets from the annular clearance; and wherein actuation of the rotor is affected by electrical current flow through the motor stator to generate a magnetic flux field that extends across the leakage flow path to displace the one or more rotor magnets to achieve rotational motion of said rotor.

17. The apparatus of claim 16, wherein said rotor is primarily suspended in the radial direction within said housing by hydrodynamic thrust forces generated by relative movement of said rotor with respect to and within said pump housing.

18. The apparatus of claim 16:
wherein said radial bearing comprises a plurality of lands protruding radially from the inner bearing surface; and
wherein the plurality of lands are spaced apart across a circumference of the cylindrical bore.

19. The apparatus of claim 16, wherein said axial bearing is configured to provide additional stability and flow characteristics to the rotor.

20. The apparatus of claim 16, wherein said one or more cylindrical bores of said pump housing comprise two cylindrical bores of differing diameters.

* * * * *